(12) United States Patent
Levit et al.

(10) Patent No.: US 11,712,540 B2
(45) Date of Patent: Aug. 1, 2023

(54) DELIVERY DEVICES, SYSTEMS AND METHODS FOR DELIVERING THERAPEUTIC MATERIALS

(71) Applicant: Emory University, Atlanta, GA (US)

(72) Inventors: Rebecca Levit, Atlanta, GA (US); Peter Campbell, Santa Clara, CA (US)

(73) Assignee: Emory University, Atlanta, GA (US)

(*) Notice: Subject to any disclaimer, the term of this patent is extended or adjusted under 35 U.S.C. 154(b) by 696 days.

(21) Appl. No.: 15/519,040

(22) PCT Filed: Oct. 13, 2015

(86) PCT No.: PCT/US2015/055255
§ 371 (c)(1),
(2) Date: Apr. 13, 2017

(87) PCT Pub. No.: WO2016/061055
PCT Pub. Date: Apr. 21, 2016

(65) Prior Publication Data
US 2017/0216561 A1     Aug. 3, 2017

Related U.S. Application Data

(60) Provisional application No. 62/135,977, filed on Mar. 20, 2015, provisional application No. 62/063,026, filed on Oct. 13, 2014.

(51) Int. Cl.
*A61M 25/00* (2006.01)
*A61M 25/04* (2006.01)

(52) U.S. Cl.
CPC ........ *A61M 25/0082* (2013.01); *A61M 25/00* (2013.01); *A61M 25/007* (2013.01);
(Continued)

(58) Field of Classification Search
CPC ...... A61M 2025/0096; A61M 25/0082; A61M 25/007; A61M 2025/0163
See application file for complete search history.

(56) References Cited

U.S. PATENT DOCUMENTS 4,902,276 A * 2/1990 Zakko ............... A61M 1/85
604/28
5,478,309 A 12/1995 Sweezer et al.
(Continued)

FOREIGN PATENT DOCUMENTS

CN    103961788    8/2014
CN    203790412 U  8/2014
(Continued)

OTHER PUBLICATIONS

English translation of Ishii.*
(Continued)

*Primary Examiner* — Courtney B Fredrickson
(74) *Attorney, Agent, or Firm* — Meunier Carlin & Curfman LLC

(57) ABSTRACT

Delivery devices, systems, and methods may be configured to define a barrier region at a treatment site to deliver one or more therapeutic materials. A device for delivering one or more therapeutic materials to a treatment site may include a body; one or more members that are movable with respect to the body and that are configured to define a barrier region at the treatment site; and one or more delivery lumens configured to deliver one or more therapeutic materials to the barrier region.

19 Claims, 30 Drawing Sheets

(52) U.S. Cl.
CPC ........ *A61M 25/0032* (2013.01); *A61M 25/04* (2013.01); *A61M 2025/0096* (2013.01); *A61M 2210/125* (2013.01)

(56) References Cited

U.S. PATENT DOCUMENTS

| | | | |
|---|---|---|---|
| 6,508,789 B1* | 1/2003 | Sinnott | A61M 25/0097 604/164.01 |
| 6,692,458 B2 | 2/2004 | Forman et al. | |
| 7,097,643 B2* | 8/2006 | Cornelius | A61B 18/1492 128/898 |
| 7,101,362 B2* | 9/2006 | Vanney | A61B 18/1492 600/152 |
| 8,088,103 B2 | 1/2012 | Teeslink et al. | |
| 8,460,181 B2* | 6/2013 | Saadat | A61B 1/00085 396/17 |
| 9,623,178 B2* | 4/2017 | Krebs | A61M 1/0084 |
| 2004/0249295 A1 | 12/2004 | Ueno et al. | |
| 2005/0004516 A1* | 1/2005 | Vanney | A61N 1/056 604/95.05 |
| 2005/0261663 A1* | 11/2005 | Patterson | A61M 25/008 264/632 |
| 2006/0200079 A1* | 9/2006 | Magnusson | A61M 25/0017 604/164.1 |
| 2006/0206096 A1 | 9/2006 | Accisano et al. | |
| 2010/0185140 A1* | 7/2010 | Kassab | A61M 25/0084 604/28 |
| 2011/0098682 A1* | 4/2011 | Ahmed | A61M 25/04 604/544 |
| 2012/0245512 A1* | 9/2012 | Fallin | A61M 25/0074 604/28 |
| 2013/0165744 A1* | 6/2013 | Carson | A61M 1/0082 600/34 |
| 2014/0005595 A1 | 1/2014 | Taylor et al. | |
| 2016/0199625 A1* | 7/2016 | Rosenbaum | A61M 27/00 604/540 |

FOREIGN PATENT DOCUMENTS

| | | | | |
|---|---|---|---|---|
| JP | 2012000390 | | 1/2012 | |
| WO | WO-9012570 A1 * | | 1/1990 | |
| WO | 0009185 A1 | | 2/2000 | |
| WO | 03033050 | | 4/2003 | |
| WO | 2004030718 | | 4/2004 | |
| WO | WO-2009073918 A2 * | | 6/2009 | ........ A61M 25/0067 |
| WO | 2011008758 A2 | | 1/2011 | |
| WO | 2011043965 A1 | | 4/2011 | |
| WO | 2013142333 | | 9/2013 | |
| WO | WO-2014006738 A1 * | | 1/2014 | ........ A61M 25/0074 |

OTHER PUBLICATIONS

International Search report and Written Opinion issued for Application No. PCT/US2015/055255, dated Dec. 30, 2015.
International Preliminary Report on Patentability issued for Application No. PCT/US2015/055255, dated Apr. 18, 2017.
Supplementary Search Report issued for European Application No. 15850325, dated Apr. 3, 2018.
English Translation of Office Action issued in Japanese Application No. 2017-519265, dated Aug. 29, 2019.
Examination Report issued for Australian Application No. 2015333792, dated Jul. 2, 2019.
English Summary of Second Office Action for Chinese Application No. 2015800555385 dated Jun. 3, 2020.
Communication pursuant to Article 94(3) EPC for European Application No. 15850325.0 dated Jun. 17, 2020.
First Examination Report issued for Indian Application No. 201717016158, dated Aug. 27, 2020.
English summary of Office Action for Chinese Application No. 2015800555385 dated Jan. 19, 2021.
Office Action issued for European Application No. 15850325.0 dated Mar. 23, 2021.
Office Action issued in corresponding Canadian Application No. 2,964,351, dated Aug. 17, 2022.

* cited by examiner

600

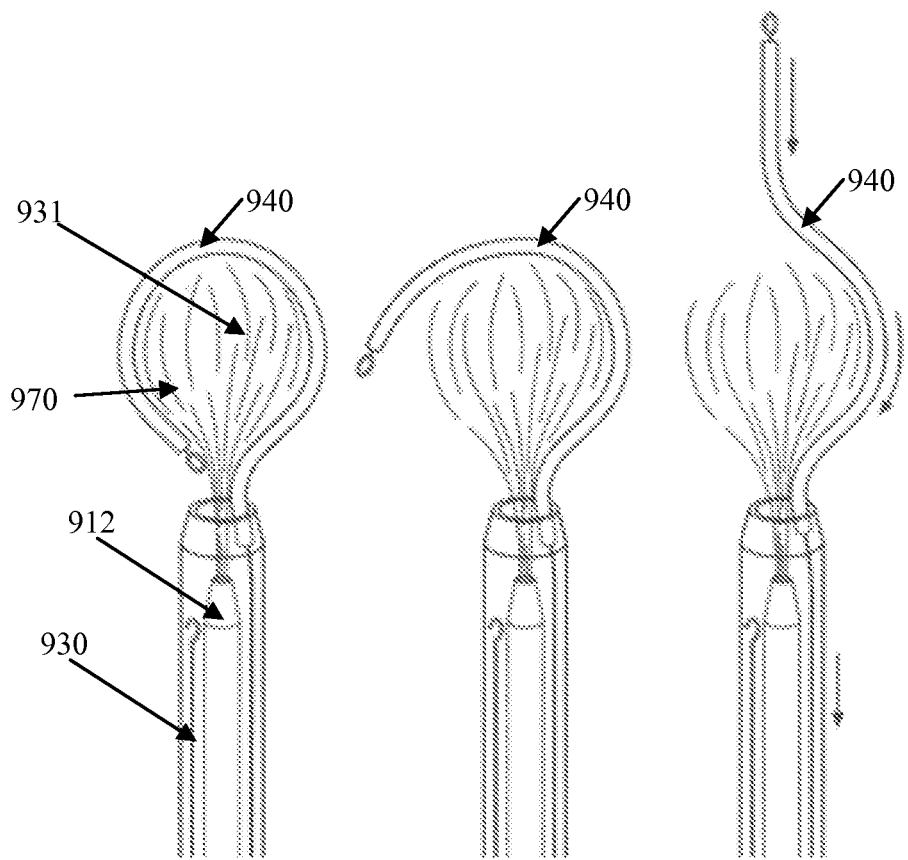
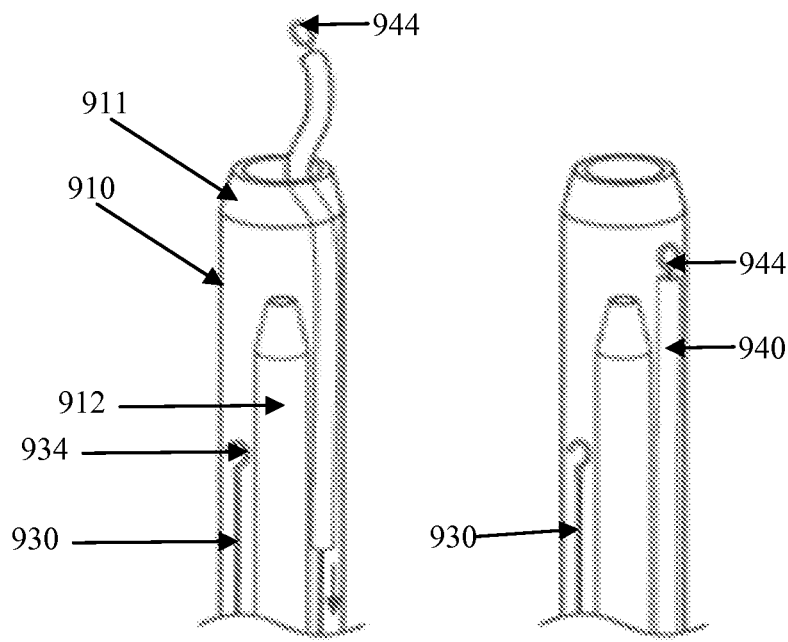
FIGURE 9B     FIGURE 9C     FIGURE 9D
FIGURE 9E     FIGURE 9F

1300

DELIVERY DEVICES, SYSTEMS AND METHODS FOR DELIVERING THERAPEUTIC MATERIALS

CROSS-REFERENCE TO RELATED APPLICATIONS

This Application is the National Stage of International Application Number PCT/US2015/055255 filed Oct. 13, 2015, which claims priority to U.S. Provisional Application No. 62/135,977 filed Mar. 20, 2015 and U.S. Provisional Application No. 62/063,026 filed Oct. 13, 2014. The entirety of each of these applications is hereby incorporated by reference for all purposes.

BACKGROUND

Extensive research has been done in the delivery of therapeutic materials, such as stem cells, cytokines, micro RNAs, and others, to regenerate or repair damaged hearts. The current standard delivery techniques have resulted in the poor retention of the therapeutic materials in the heart. These techniques include intracoronary injection, intramyocardial injection at the time of open heart surgery, or intramyocardial injection using catheter systems (such as NOGA) from within the left ventricle. Using these techniques, most therapeutic materials are rapidly washed out via the existing capillary or lymphatic systems, expelled into the ventricle, or fail to engraft in the heart muscle due to the inhospitable environment. Thus, the effectiveness of the therapeutic materials can be limited by poor retention in the heart due to mechanical wash out or degradation.

Recent pre-clinical research has focused on delivering therapeutic materials on scaffolds of bio-compatible materials to the heart to improve retention. These composite "patches" can improve retention of transplanted cells the therapeutic materials in the heart by providing a more hospitable environment as well as reducing washout via capillary and lymphatic channels. These composite patches can also direct cell activity and send molecular signals to the cells. Biomaterials can also act as scaffolds to localize therapeutic materials to a target area and/or in a sustained release manner. However, delivery of biomaterials to the heart by traditional methods typically requires open heart surgery. Additionally, traditional delivery techniques may not be safe because they could result in an embolism that could cause heart attacks and strokes, and intramyocardial delivery techniques could cause cardiac arrhythmias.

SUMMARY

Thus, there is a need for an effective, less invasive and safe delivery of therapeutic materials to a region, such as the heart.

The disclosure relates to delivery devices, systems, and methods for delivering therapeutic material (s) without requiring invasive heart surgery. These devices, systems, and methods may allow delivery of bio-material embedded stem cells, cytokines, drugs, biologics, as well as other advanced therapeutics to the heart, for example, via the pericardium. This can allow the therapeutic materials to be delivered in a specific anatomic position (anterior wall, posterior wall, lateral wall) and also allow for adjustment of the size of the patch formed by the bio-material embedded therapeutic material. The delivery device can be temporarily left in place for minutes to days to allow gelation and/or engraftment of the delivered therapeutic materials.

In some embodiments, the devices may relate to a device for delivering one or more therapeutic materials. In some embodiments, the device may include a body and one or more members that are movable with respect to the body. In some embodiments, the one or more members may be configured to connect and/or overlap with respect to the one or more members and/or the body to define a barrier region at the treatment site. In some embodiments, the one or more delivery lumens may be configured to deliver one or more therapeutic materials to the barrier region.

In some embodiments, a device may include a body and at least one member that is movable with respect to the body. The at least one member may be configured to define a barrier region at the treatment site. The one or more members may include at least one set of one or more ports disposed on a surface of at least one member and configured to deliver suction. The one or more members may include at least one set of delivery ports disposed on a surface of the at least one member so that the ports surround the barrier region and configured to deliver at least one therapeutic material.

In some embodiments, a device for delivering one or more therapeutic materials to a treatment site may include a body. The device may further include at least two members that are configured to move between an elongated state and a radially expanded state. The radially expanded state may include the at least two members radially expanding with respect to the body, the at least two members in the radially expanded state defining a barrier region at the treatment site. In some embodiments, the device may include one or more delivery lumens configured to deliver one or more therapeutic materials to the barrier region.

In some embodiments, the methods may include a method for delivering one or more therapeutic materials within a pericardium space. In some embodiments, the method may include advancing one or more members into the pericardium space through a body of a device. The method may include forming a barrier region within the pericardium space by connecting or overlapping the one or more members with respect to the one or more members and/or the body. The method may also include delivering one or more therapeutic materials to the barrier region.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIGS. 9A-F show operation of a delivery device according to embodiments;

DETAILED DESCRIPTION OF THE EMBODIMENTS

Figure 1:
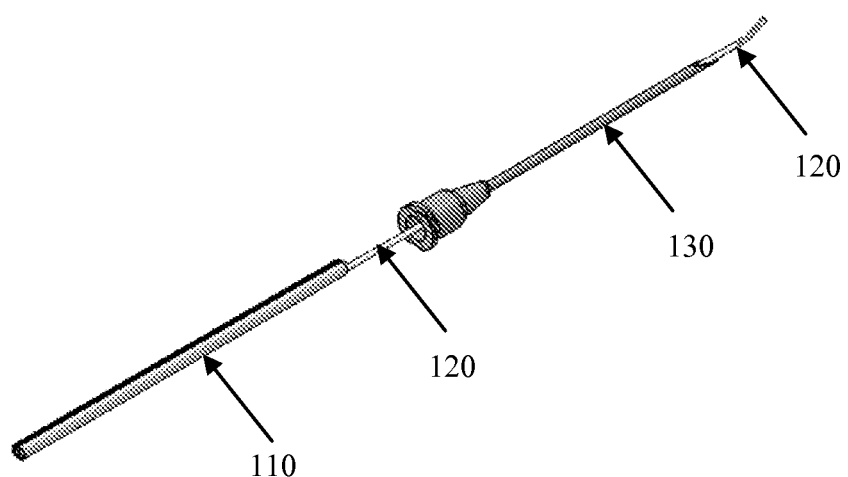
FIG. 1 shows a delivery system according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications.

The terms "distal" and "proximal" used herein with respect to the delivery device and features are with respect to the position of the delivery device when in use. "Distal" indicates an end of the delivery device or a feature of the device closest to, or a direction towards the treatment site, and "proximal" indicates an end of the device or a feature of the device farthest from, or a direction away from the treatment site. "Treatment site" refers to any site or region of a subject, human or animal, intended to be treated, such as a tissue of an organ or muscle. Although the treatment site is discussed with respect to the pericardium space, it will be understood that the treatment site may be other regions, for example, other regions in and/or near the heart, regions in and/or near other organs (e.g., lungs, liver, brain, etc.), vasculature, joint spaces, among others, or a combination thereof. It is also understood that the delivery devices, systems, and methods according to embodiments could be used for delivery of diagnostic or therapeutic materials.

The delivery devices, systems and methods according to embodiments may be configured to deliver one or more therapeutic materials in a region defined by the device (referred to as "defined barrier region"). This can enable accurate placement of the one or more therapeutic materials at a treatment site. Also, the device may remain at the treatment site for a period of time until the one or therapeutic materials gelate and/or engraft in the defined barrier region; and thereby can improve retention of the one or more therapeutic materials.

The "therapeutic material" may include any one or more substance, compound, composition, formulation, and/or agent capable of exerting an effect, such as a therapeutic, prophylactic or diagnostic effect, on a patient; and/or medium configured to deliver such material. Examples of therapeutic materials include but are not limited to stem cells, cytokines, biologics, drugs, micro RNAs, among others, or a combination thereof. The medium may be a bio-absorbable medium configured to deliver a therapeutic agent or material. By way of example, the medium may be any material that can cause the agent to gelate and/or engraft. In some embodiments, the devices may include more than one lumen to deliver the same therapeutic material(s), separately deliver different therapeutic materials and/or converge at some point to deliver a combination of one or more therapeutic materials. The multiple lumens may be of different and/or same size, shape and/or location, or a combination thereof, within the device.

In some embodiments, the delivery devices may be a catheter-like device. The delivery devices may include a (sheath) body and one or more members configured to move with respect to the body. The one or more members may be configured to define a barrier region at a treatment site in which one or more therapeutic materials can be delivered. In some embodiments, the body and/or the one or more members may include one or more lumens.

In some embodiments, the body, the one or more members, and/or the one or more lumens may have any dimensions (e.g., length and/or diameter) and/or shape. The body, the one or more members, and/or the or more lumens may be adjusted and sized for the anatomy, the direction of the desired point of insertion, the material(s) to be delivered, among others, or a combination thereof. For example, the body may be sized for insertion into a vascular lumen (e.g., 1.0-2.0 mm in diameter). The body, the one or more members and/or the one or more of lumens may also be adjusted according to the requirements of the therapeutic materials to be delivered to the patient.

In some embodiments, the body may have a first end (also referred to as proximal end), an opposing second end (also referred to as distal end), and a length therebetween. In some embodiments, the body may have a symmetric, elongated shape. In some embodiments, the body may have an asymmetric, elongated shape, for example, to prevent rotation/rolling of the device while at the treatment site (e.g., in the heart while in the pericardium). In some embodiments, the body may have a tapered tip disposed at the distal end.

In some embodiments, the body and/or one or more members may include one or more surface members configured to enhance flexibility and/or favor curling in a direction. For example, in some embodiments, the body and/or one or more members may include a plurality of serrations and/or slots disposed at least partially along the length. The serrations and/or slots may have any pattern, shape, size, or depth.

In some embodiments, the body may include one or more stabilizing members disposed adjacent to the distal end at least partially along the length. The one or more stabilizing members may be configured to communicate with the surrounding tissue at a treatment site so as to stabilize the body when the one or more members is moved with respect to the body. In some embodiments, the one or more stabilizing members may include ports configured to deliver suction provided by a vacuum source, suction cups, needles, spikes, spurs, other protruding members, among others, or a combination thereof. The one or more stabilizing members may have any number, size, shape, pattern, among others, or a combination thereof.

In some embodiments, the delivery device may include any number of members. In some embodiments, the delivery device may include one member, two members, three members, four members, etc. In some embodiments, the one or more members may be configured to connect to and/or overlap (e.g., curl) with respect to itself, another member and/or the second (distal) end of the body so as to define the region by a treatment site. The connected or overlapped state of the member(s) may be referred to as the "closed" state. By way of example, in the connected or overlapped state of the members, the member can surround an area at a treatment site (e.g., the pericardium space). In this way, the member(s) can act like a boundary of (e.g., a fence around) an area at a treatment site, for example, in the pericardium space and thereby form a restricted area at the treatment site (e.g., the barrier region defined by the member(s)) in which the therapeutic material can be delivered. During delivery and/or in the expanded form, the region may have any shape. In some embodiments, the region may circular shape, ovoid shape, D shape, etc., among others.

In some embodiments, the size and/or shape of the region may be adjustable, for example, by further advancing or deploying the one or more members with respect to the distal end (send end) of the body. In this way, the size and/or the shape of the region may depend on an amount of advancement or deployment of the one or more members with respect to the end of the body. In some embodiments, the size and/or shape of the region may be predefined. For example, the inflection and/or radius of curvature may be predefined. In some embodiments, one or more members may each have one point of inflection, two points of inflection, among others, or a combination thereof.

In some embodiments, the one or more members may include one or more external markings disposed on the outside surface. In some embodiments, the markings may indicate depth and/or length.

In some embodiments, the one or more members may be made of biocompatible materials. The materials may be stiff, flexible and/or semi-flexible. The materials may include but are not limited to plastic, shape memory alloy (e.g., nickel Titanium, Nitinol® or high tempered spring steel) rubber, composites, metals, fibers, other synthetic materials, other biological materials, among others, or a combination thereof. The materials may include, for example, single compound polymer or composite reinforced structure such as a braided or coiled layer of metal (such as steel), fiber (such as Kevlar or nylon), embedded within a polymer (such as Polyether block amide, Nylon, or Polyolefin), elastomer (such as Polyurethane), or fluoropolymer (such as Polytetrafluoroethylene).

In some embodiments, the one or more members may be configured to constrain the one or more therapeutic materials to the defined barrier region in multiple directions, for example, laterally and/or vertically with respect to a treatment site. In some embodiments, the one or more members may be configured to act a "roof" and "walls" of the defined barrier region.

In some embodiments, the one or more members and/or the body may include one or more sets of one or more ports configured to deliver suction provided by a vacuum source. For example, the one or more ports may be configured to cause the surrounding tissue to removably adhere to the one or more surfaces of the one or more members and/or the body. For example, for the pericardium space, the one or more ports may cause the pericardial and/or epicardial tissues to adhere to the one or more surfaces of the one or more members and/or the body when suction is applied. For example, the body may include one or more set of ports disposed on one side of the one or more members and/or the body to communicate with the pericardial tissue and/or one more sets of ports disposed on another side of the one or more members and/or the body to communicate with the epicardial tissue. When suction is applied, the pericardial and/or epicardial tissue adhered to the one or more members may act as a "roof" and the one or more members may act as the walls of the defined barrier region. In some embodiments, the ports may be configured to cause the overlapped portions of the one or more members to adhere to each other. In this example, the one or more members may act as the walls of the defined barrier region.

In some embodiments, the delivery devices may additionally and/or alternatively include one or more constraining members that are disposed on the surface of the one or more members and extend from a surface of the one or more members to within the defined barrier region. In some embodiments, the one or extending members may be disposed on at least one surface of the one or more members. In some embodiments, the one or more constraining members may be configured to at least to partially cover the bottom and/or top surfaces of the one or more members. The one or more constraining members may act as a "roof" and the one or more members may act as the walls of the defined barrier region.

In some embodiments, each of the one or more constraining members may be of the same material, same dimensions, different material, different dimensions, or a combination thereof. In some embodiments, the one or more constraining members may be substantially the same material as the one or more members. In some embodiments, each of the one or more members may include the same and/or different constraining member. By way of example, a member may include a constraining member disposed on one surface (e.g., bottom surface and/or top surface) and a constraining member disposed on the opposite surface (e.g., top surface and/or bottom surface), and one of these constraining members extends further into the defined barrier region than the other constraining member.

In some embodiments, the delivery devices may include one or more steering members configured to be disposed within the one or more members. The steering members may be a wire-like member configured to mechanically and/or electrically control the movement of the one or more members, for example, by axial or torsional driven mechanisms with respect to the body. In some embodiments, the one or more steering members may be formed of a shape memory alloy (e.g., Nitinol) and therefore may be configured to control the shape of one or more members according to the shape defined by the shape memory alloy. By way of example, the one or more steering members can cause the one or more members to curve or inflect according to the shape defined by the shape memory alloy and thereby cause the one or more steering members to overlap and/or connect to define the barrier region.

In some embodiments, the one or more steering members may be configured to cause the one or more members to overlap with each other so as to define the barrier region at a treatment site. For example, the one or more steering members may cause a member to curl in a single plane so that the portion of a member overlaps with respect to itself (e.g., another portion of the member) so to form the defined region when the member is caused to be deployed through the body. In this way, by overlapping in a single plane, the member may substantially seal the barrier region to substantially minimize and/or prevent leakage of a therapeutic material at the treatment site.

In some embodiments, the delivery devices may additionally and/or alternatively include one or connecting members disposed on the body, the one or more members, and/or the one or more steering members. The one or more connecting members may be configured to connect to itself, another member and/or the second end of the body so as to define the barrier region at a treatment site.

In some embodiments, the one or connecting members may be different and/or complimentary connecting members. The connecting member(s) may include but are not limited to mechanical connecting members (e.g., hook and eye, tongue and groove, barb and cavity, interlocking C clefts, suture with retractable knot, other latching members, etc.), magnetic or electromagnetic connecting members (e.g., ball in socket), material connecting members (e.g., "tacky seal" using low durometer polymers or elastomers (such as Shore 50A-90A or 20D-50D)), members configured to deliver pressure (e.g., bio-absorbable tips, suction, etc.), among others, or a combination thereof.

In some embodiments, the one or more connecting members may be configured to connect to substantially seal the barrier region. The substantial seal between connecting member(s) may be a connection in which leakage of a therapeutic material can be substantially minimized and/or prevented.

In some embodiments, the delivery device may include one or more connection points disposed on the body and/or the one or more members at which the connecting members may connect. The one or more connection points may be include but are not limited to within the body, at apex of the defined region, and other locations along the defined region. By way of example, for devices having at least two members and/or two connecting members may expand symmetrically so that they connect at the apex and/or expand asymmetrically (e.g., one member and/or connecting member may be longer than the other member and/or connecting member) so that they connect at other locations.

In some embodiments, the delivery devices may be configured to release the closed state of the one or more members. In some embodiments, the closed state (e.g., connected or overlapped) state may be configured to be released, for example, by a retraction of hook, cutting suture, rotation c cleft, retraction of a steering member and/or other mechanical part(s), disruption of magnetic field by electric current, and/or disruption of suction. In some embodiments, the connecting members can be configured to be disrupted and re-instated once, twice, or more times.

In some embodiments, the one or more members may be configured to be deployed through the body in a generally elongated or opened state, in a connected or a closed state (e.g., the connecting members (e.g., connected or overlapped) or a combination thereof. In some embodiments, if the one or more members are deployed in an elongated or opened state, the one or more members may be configured to be caused to be in the closed state (e.g., in an overlapped or connected state) after advancing the one or more members with respect to the body to a certain point, for example, via the one or more steering members. By way of example, the point at which the one or more members are configured to be in a closed state may be preset by the shape memory allow included in the one or more members and/or steering members.

In some embodiments, the one or more lumens may be disposed at least partially along the length of the body and/or along the length of the one or more members. In some embodiments, the one or more lumens may extend from the first end to the second (distal) end of the body and/or the one or more members. In other embodiments, the one or more lumens may extend from a position along the length of the body and/or one or more members to about the second (distal) end. In some embodiments, the one or more lumens may be of the same and/or different dimensions, shape, length, or a combination thereof.

In some embodiments, the one or more lumens may include one or more delivery lumens configured to deliver one or more therapeutic materials. The devices may include any number of delivery lumens. In some embodiments, the devices may include one delivery lumen. In other embodiments, the devices may include more than one delivery lumen (e.g., two lumens, three lumens, four lumens, etc.). In some embodiments, the device may include at least two delivery lumens configured to deliver one or more therapeutic materials. In some embodiments, the more than one delivery lumen may be of the same and/or different dimensions, shape, length, or a combination thereof.

In some embodiments, the one or more delivery lumens may be disposed within the one or more members. In this example, the one or more members may include one or more sets of a plurality of delivery ports configured to deliver one or more therapeutic materials to the defined region. In some embodiments, the delivery ports may be of any number, shape, pattern, spacing, or a combination thereof. In some embodiments, the ports include but are not limited to symmetric openings, angled openings, among others, or a combination thereof. In some embodiments, the delivery ports may be disposed along a portion of the length of the one or more members. By way of example, the delivery ports may be disposed on one or more surfaces of the one or more members, one or more regions of the one or more members, or a combination thereof. For example, the ports may be disposed in a pattern along a region or opposing regions of the one or more members that can facilitate gelation and/or mixing of the delivered therapeutic material(s). For example, the delivery ports may be disposed on a surface or side of the one or more members so as to surround or border the defined region so that the ports deliver the material to the defined area. By way of another example, one or more members may include at least two sets of one or more delivery ports, each set being configured to communicate with a delivery lumen.

For more than one delivery lumen, each lumen may be configured to deliver a different therapeutic material. In some embodiments, the delivery lumens may extend along separately within the body and/or the one or more members so that each lumen separately delivers a therapeutic material (e.g., via a set of delivery ports). In other embodiments, the lumens may converge along the length of the body and/or one or more member so to allow mixing of the therapeutic materials within the body.

In some embodiments, the delivery lumen(s) may be disposed parallel, angled, or a combination thereof, with respect to the length of the body and/or the one or more members. In some embodiments, the one or more delivery lumens may have a diameter that is substantially the same along its length, may have a diameter that is asymmetric along the length, or a combination thereof. In some embodiments, one or more of the delivery lumens may have spirals within its orifice configured to direct and/or influence flow of the therapeutic material (e.g., gel), as well as to influence the outflow of the therapeutic material in a specific direction. In some embodiments, the one or more lumens may have an outflow shape similar to a "duckbill" valve configuration to prevent backflow back into the catheter after gel delivery.

In some embodiments, the one or more delivery lumens may be disposed in the body. In some embodiments, the first end of the one or more delivery lumens may be disposed at the first end of the body. In other embodiments, a first end of the one or delivery lumens may be disposed at a position along the body. In this example, the area for which the therapeutic material (e.g., the lumen dead space) may need to flow is minimized and thereby reducing therapeutic material waste.

In some embodiments, the one or more delivery lumens and/or one or more members may be coated with materials configured to increase the viability of cells or cytokines or to prevent therapeutic material from adhering to the walls of the lumens and/or members.

In some embodiments, the body and/or the one or more members may include one or more lumens configured for a vacuum source. In some embodiments, the body and/or the one or more members may also include one or more lumens configured for other components. In some embodiments, one or more lumens may be configured for a specific component, multiple components, or a combination thereof. In some embodiments, one or more components may be additionally and/or alternatively disposed on the (surface) of the body and/or the one or more members.

In some embodiments, the components may include but are not limited to one or more electrical components (e.g., ultra violet (UV) light generation to facilitate gelation, sensors, fiberoptics, etc.), imaging devices (e.g., camera, intravascular ultrasound, intracardiac echocardiography, etc.), steering components (e.g., guide wire), sampling/biopsy components (e.g., to sample pericardial fluid), among others, or a combination thereof. In some embodiments, the sensors may include any sensors. For example, for the pericardium space, the sensors may include any sensors configured to detect, monitor, and/or alter the electrical activity of the heart. By way of example, the sensors may include voltage sensors configured to detect electrical activity and thereby detect scar tissue, pressure sensors configured to intrapericardial pressure, motion or flow sensors to detect coronary artery or vein blood flow.

It will be understood that the delivery devices according to the embodiments may be implanted into a patient with use of a delivery system. The delivery devices may be a part of the delivery system. FIG. 1 shows a delivery system 100 according to embodiments. As shown in FIG. 1, the system 100 may include a delivery device 110, a guide wire 120, and a needle 130. The delivery system 100 may also include a handle assembly (not shown). The delivery system 100 is not limited to those shown in the figures and the delivery devices according to embodiments may be used with other delivery systems. It will also be understood that a clinician may use a delivery system to control the operation of the disclosed delivery devices. It will be further understood that although the operations of the disclosed delivery devices are discussed with respect to the actions of a clinician, delivery systems may be configured to perform these actions.

For example, for delivery of one or more therapeutic materials to the pericardium space, a clinician may direct the needle 130 to the pericardium space. To gain access to the pericardium space, a clinician may use any known invasive and less invasive approaches to the heart. The approaches may include but are not limited to subxyhpoid, trans-apical, parasternal/intercostal, surgical (e.g., sternotomy, thoracotomy, mini-sternotomy, Davinci robotic system, etc.), image-guided (e.g., ultrasound guidance, fluoroscopy, CT, MRI, ICE, etc.), etc. After the needle is positioned within the pericardium space, a clinician may then use the guide wire 120 to the pericardium space and remove the needle 130. The clinician may then move the device 110 into the pericardium space using the guide wire 120.

In some embodiments, the delivery system 100 may also include a sheath to guide and/or direct the guide wire 120. In some embodiments, the sheath may have an angled or curved shape configured to direct the guide wire 120 and/or one or more members before and/or during the procedure. If the device include sheath, the clinician may move the sheath with the device 100 using the guide wire 120 or may move the sheath in place, remove the guide wire 120, and advance or deploy the device 110 into the pericardium.

FIGS. 2 through 16 show examples of the delivery devices configured to define a barrier region for delivery of one or more therapeutic materials. It will be understood that the delivery devices are not limited to the configuration and/or combination of the body, one or more members, port(s), steering member(s), lumen(s), and/or one or more connecting members shown in and described with respect to the figures. The delivery devices may include any combination of embodiments. It will also be understood that the devices may include additional lumens, for example, for sensing pressure within the delivery space or sampling biological fluids.

FIGS. 2 through 6 and 13 through 16 show a delivery device having one member configured to define a barrier region in which one or more therapeutic materials can be delivered according to embodiments.

FIGS. 2A-2E show a delivery device 200 with a member configured to define a barrier region by a magnetic connection. As shown in FIGS. 2A-E, the delivery device 200 may include a member 230 configured to define a barrier region 231 in which one or more therapeutic materials may be delivered. The device 200 may include a body 210. In some embodiments, the body 210 may include a first (distal) end 211 and a second (proximal) end 213 and a length therebetween.

In some embodiments, the member 230 may be retractable and/or advanceable or deployable with respect to the body 210 and configured to define a barrier region 231 when advanced. In some embodiments, the region 231 may be circular. The region may also have a different shape. In some embodiments, the member 230 may include a lumen 216 and have at least one open end. In some embodiments, the device 200 may include a steering member 240 disposed within the lumen 216 configured to control the movement of the member 230 in the formation of the region 231. In some embodiments, the steering member 240 may be configured to move with and/or with respect to the member 230 within the lumen 216.

Figure 2A:
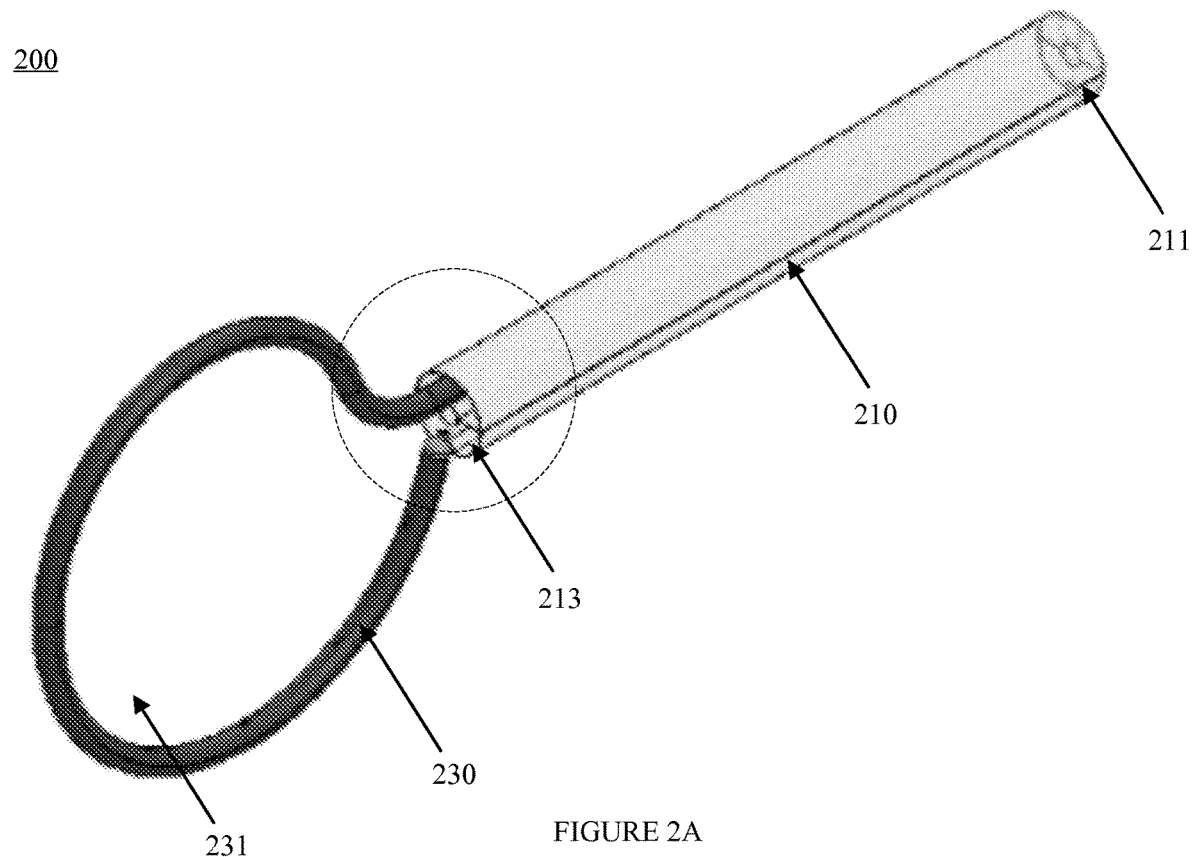
FIGS. 2A-E show views of a delivery device according to embodiments.
Figure 2B:
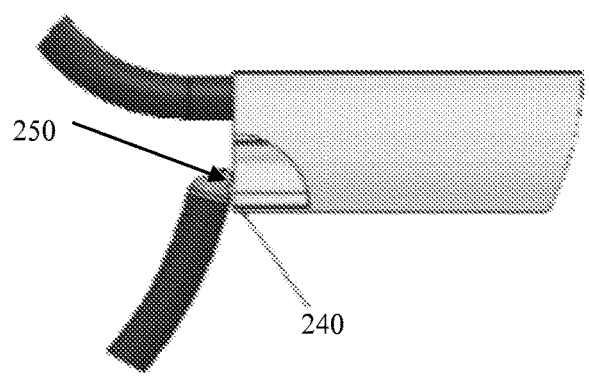
Figure 2C:
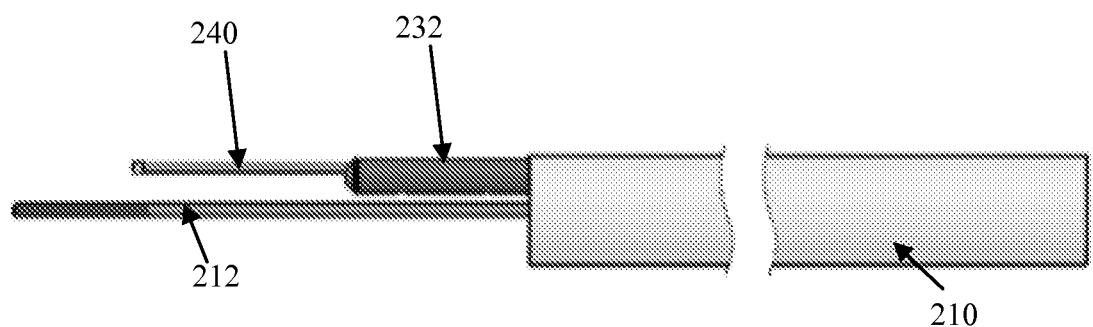
Figure 2D:
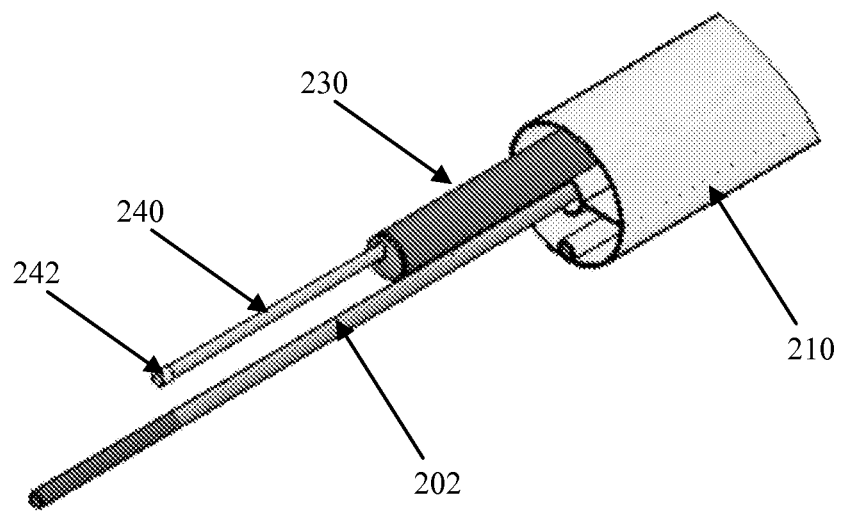

In some embodiments, the steering member 240 may include a connecting member 242 disposed at the end, as shown in enlarged view in FIG. 2B. In some embodiments, the body 210 may include a complimentary connecting member 250. In some embodiments, the connecting members 242 and 250 may be magnets of opposite polarity so that they form a magnetic connection. In this way, when the connecting members 242 and 250 are engaged, the member may be in a closed state.

In some embodiments, the connecting member 250 may be disposed at the second end 213 of the body 210. In other embodiments, the connection point may be disposed in other places. For example, the connecting member 250 may be disposed within the body 210 so that the connection body is within a lumen of the body 210.

In some embodiments, the member 230 is configured to define the region so as to surround a delivery lumen. In this way, the member 230 can form a barrier region in which one or more therapeutic materials may be delivered.

Figure 2E:
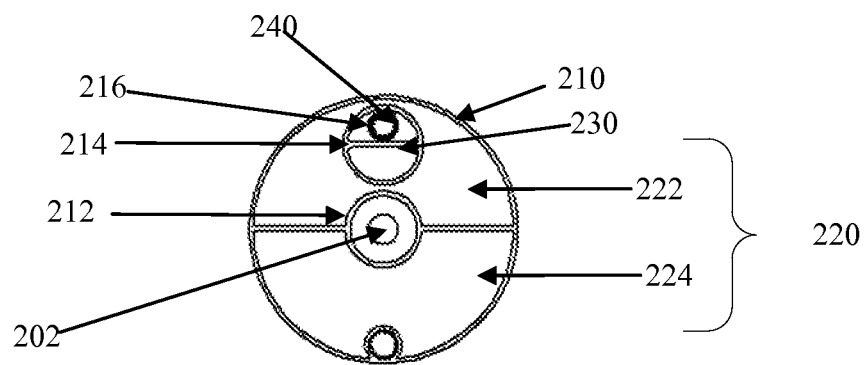

In some embodiments, as shown in the cross-section in FIG. 2E, the body 210 may include a plurality of lumens. In some embodiments, the body 210 may include a lumen 212 disposed in substantially the center of the body 210 configured for a guide wire 202. In some embodiments, the body may include a lumen 214 configured for the member 230. The body 210 may also include one or more lumens 220 for delivering one or more therapeutic materials. In some embodiments, the body may include lumens 222 and 224 for delivering the same therapeutic material and/or different therapeutic materials.

Figure 3A:
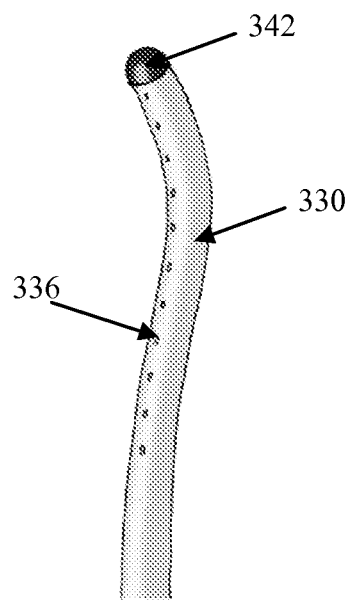
FIGS. 3A-C show operation of a delivery device according to embodiments.
Figure 3B:
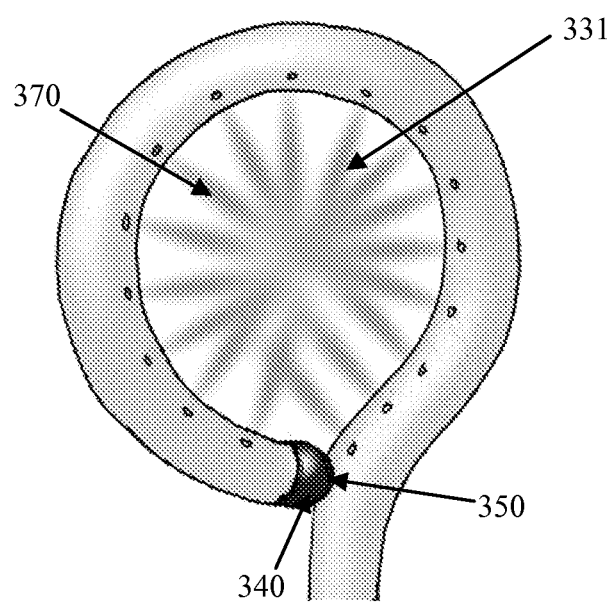
Figure 3C:
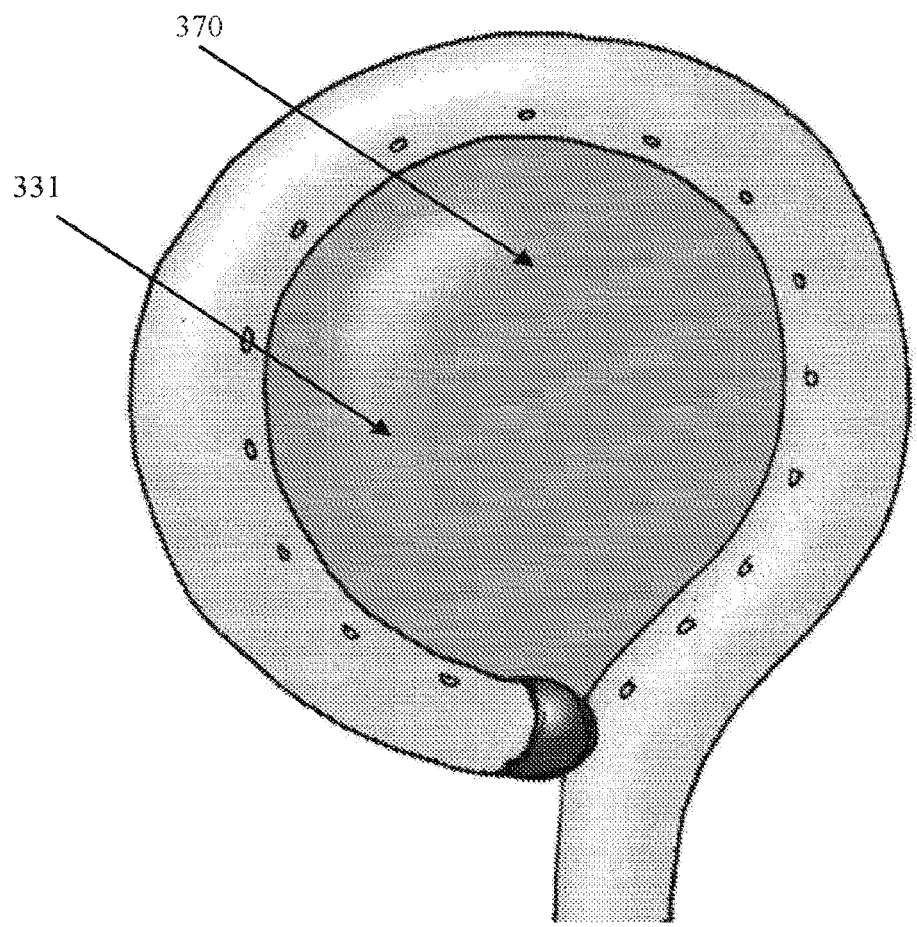

FIGS. 3A-3C show a member 330 configured to define a barrier region by connecting to a point along the length of the member 330. In some embodiments, like the member 230, the member 330 may be deployable and retractable with respect to body, and configured to define a barrier region 331 when advanced.

In some embodiments, the member 330 may include a connecting member 342 disposed at the end. The connecting member 342 may have magnetic polarity. In some embodiments, at least at one area along the length of the member 330 may have opposite magnetic polarity so that the connecting member 342 and the member 340 form a magnetic connection to define the region 331. In this way, when the connecting member 342 and the member 340 are engaged, the member may be in a closed state. In some embodiments, the member 330 may include a plurality of ports 336 to deliver one or more therapeutic materials within the defined barrier region (e.g., formed by the closed state).

In operation, the member 330 may be configured to be advanced or deployed through a body (not shown) in an elongated state (e.g., open state) and caused to curve (to form the closed state) as shown FIG. 3B by using mechanical force (e.g., a mechanical pulley system) and/or electrical force. By way of example, the member 330 may made of a shape memory alloy configured to form the shape to define the region 331. In other embodiments, the member 330 may include a steering member (not shown) configured to cause the curve shown in FIG. 3B. After the connecting member 342 magnetically connects to the member 330 to define the region 331, one or more therapeutic materials 370 may be delivered into the region 331. The member 330 may be remain within the target site until one or more therapeutic materials 370, for example, engraft and/or gelate, as shown in FIG. 3C. After which, the connection may be released, and the member 330 may be unfurled from and around the materials 370 and retracted back into the body (e.g., in the elongated or open state).

In some embodiments, one or more members may further include one or more electrical sensors configured to detect areas of variable electrical activity, such as scar. The one or more sensors may be disposed along a portion of the length of the one or more members. In this way, the sensors may be configured to detect target sites. In some embodiments, the one or more electrical sensors may be disposed at various positions along the length of the member.

Figure 4:
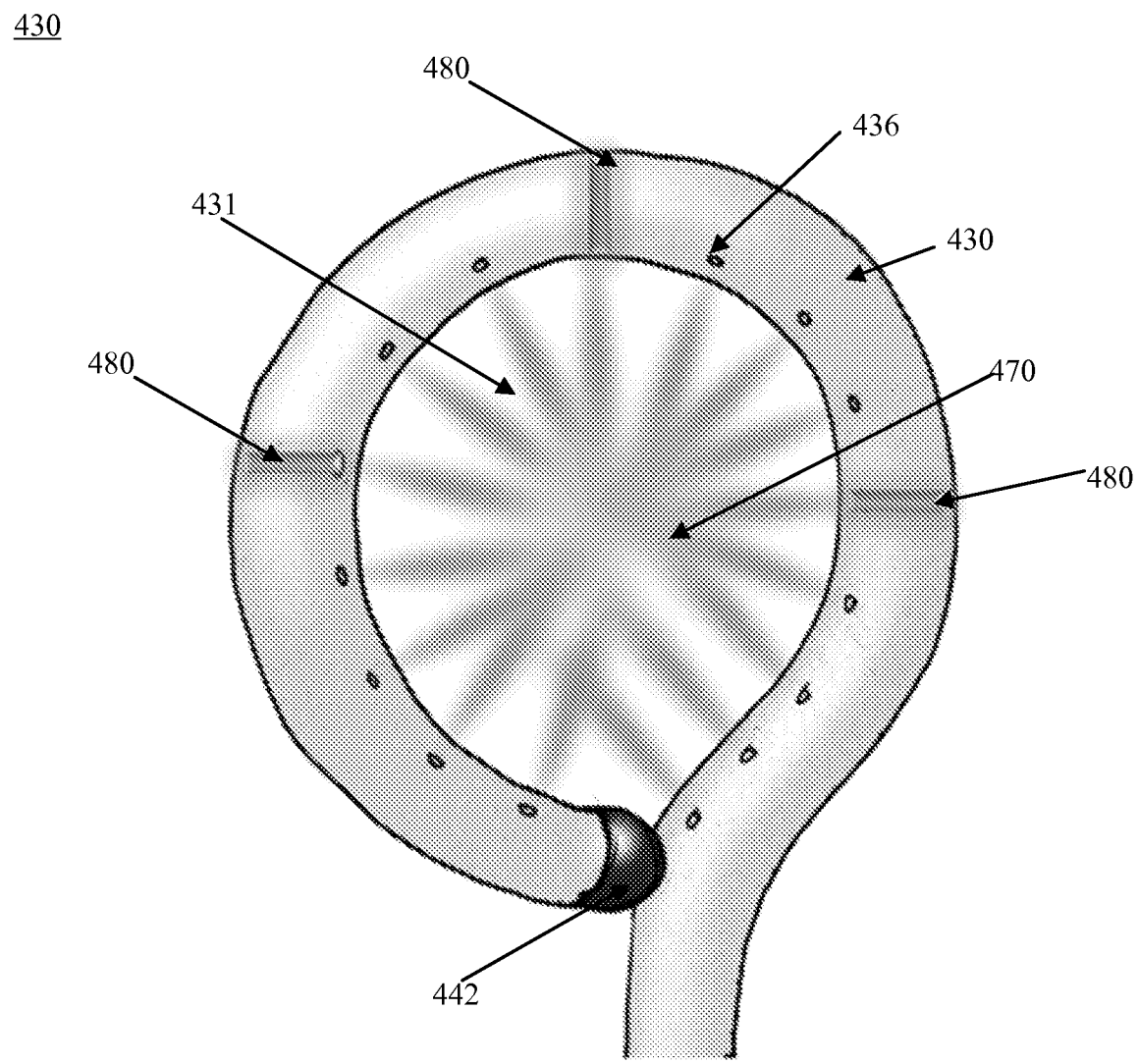
FIG. 4 shows a delivery device according to embodiments.

FIG. 4 shows a member 430 having a plurality of electrical sensors 480 disposed along the length. The member 430 may be similar to the member 330 shown in FIGS. 3A-3C. The member 430 may include a plurality of ports 436 for delivery of one or more therapeutic materials 470 into a barrier region 431 defined by a connecting member 442 configured magnetically connected a position on the member 430. It will be understood that members according to any of the embodiments discussed herein may also include electrical sensors.

Figure 5:
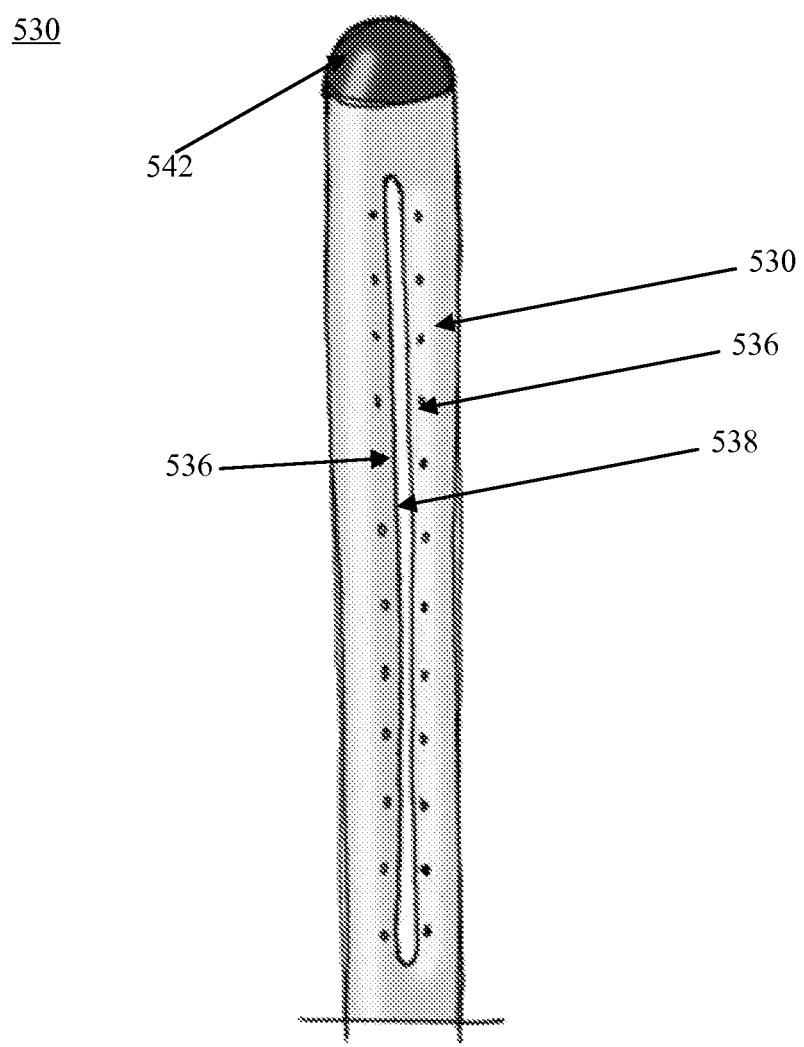
FIG. 5 shows a delivery device according to embodiments.

In some embodiments, one or more members may further include a port disposed along the length of the member for delivery of one or more therapeutic materials. FIG. 5 shows an example of a member 530 according to embodiments. The member 530 is shown similar to member 330. The member 530 may include one or more ports 536 disposed at a plurality of positions along its length, a port 538 extending at least partially along the length of the member 530, and a connecting member 542 configured to magnetically connect to a position disposed on the member 530. However, it will be understood that members according to other embodiments discussed herein may also include electrical sensors.

FIGS. 6A through 6E show a delivery device 600 with a member configured to define a barrier region by a pressure seal. Like the delivery device 200, the delivery device 600 may include a member 630 configured to define a barrier region 631 in which one or more therapeutic materials may be delivered.

In some embodiments, the device 600 may include a body 610. In some embodiments, the member 630 may be deployable and retractable with respect to the body 610 and configured to define a barrier region 631 (e.g., in a closed state) when the member 630 is advanced. In some embodiments, the member 630 may include a connecting member 642 disposed at a closed end of the member 630 and one or more lumens 616 that extends along at least partially the length of the member. In this example, the member 630 includes two lumens 616.

In some embodiments, the device 600 may include one or more steering members 640 configured to control the movement of the member 630 in the formation of the region. In some embodiments, the device 600 may include two steering members 640. In some embodiments, each steering member 640 may be configured to move with the member 630 within respective lumen 616.

In some embodiments, the member 630 may include a plurality of ports 636 for delivery of one or more therapeutic materials. In some embodiments, the ports 636 may be any number, shape, pattern, size, or spacing. In some embodiments, the ports 636 may be disposed at an angle.

In some embodiments, the member 630 may be configured to define the region by the connecting member 642 asserting pressure against a point along the member 630. In other embodiments, the member 630 may be configured to assert pressure against the body 610. Using the steering members 640 to apply pressure (e.g., mechanical force), the tip 642 can compress against the member 630 and thereby the connection can form a seal.

Figure 6A:
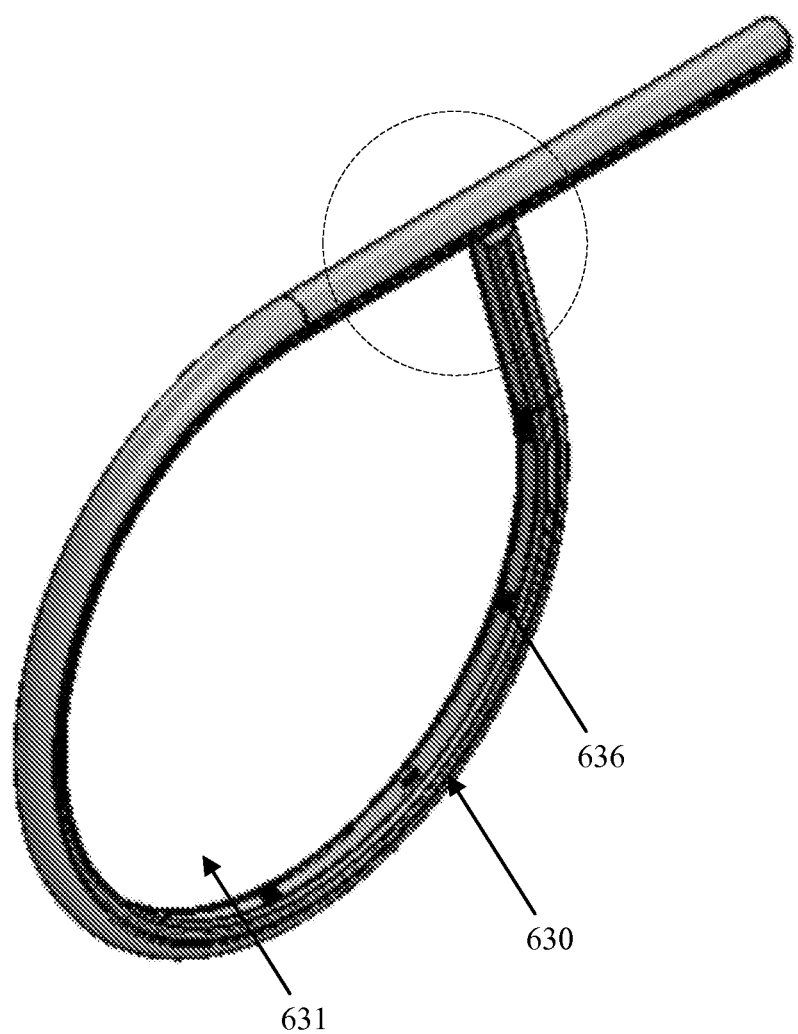
FIGS. 6A-E show views of a delivery device according to embodiments.
Figure 6B:
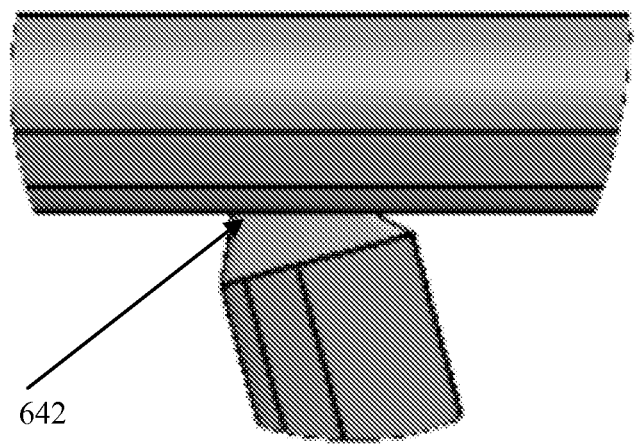
Figure 6C:
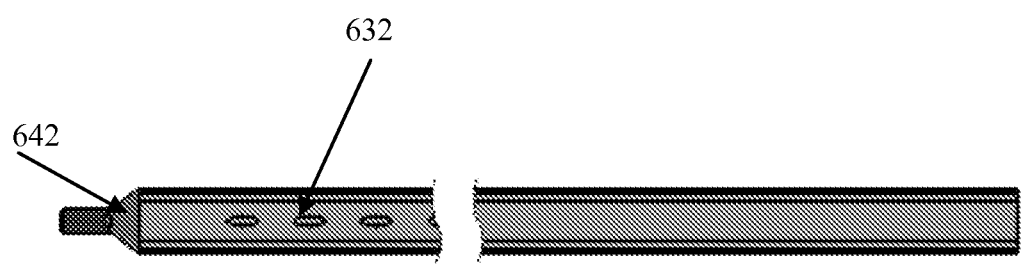
Figure 6D:
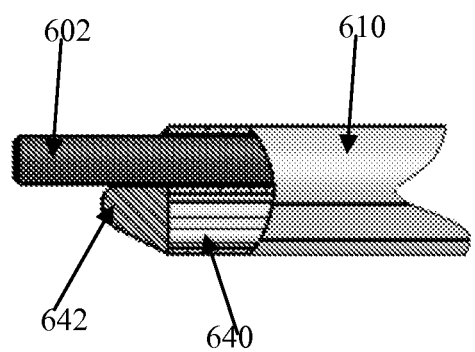
Figure 6E:
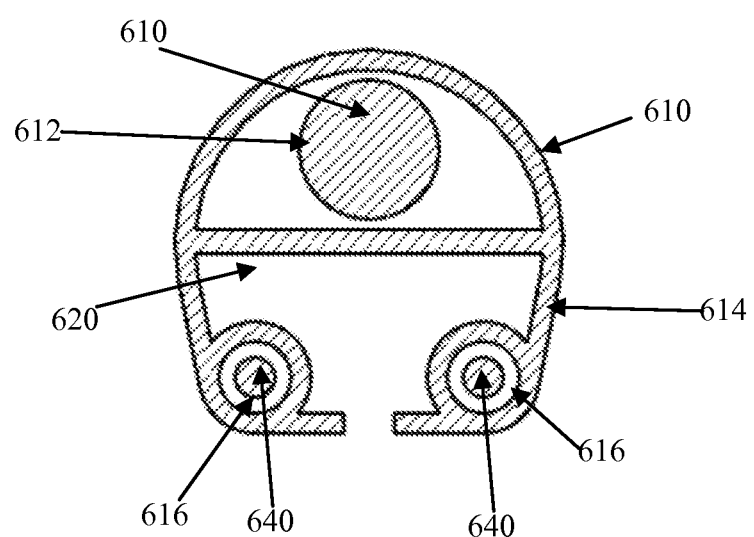

In some embodiments, as shown in the cross-section in FIG. 6E, the body 610 may include a plurality of lumens. In some embodiments, the body 610 may include a lumen 612 disposed in substantially the center of the body 610 configured for a guide wire 602. In some embodiments, the body 610 may include a lumen 614 configured for the movement of the member 630. The body 610 may also include a lumen 620 for delivering one or more therapeutic materials. In some embodiments, the lumen 620 may be divided into at least two lumens for delivering the same therapeutic material and/or different therapeutic materials.

Figure 12A:
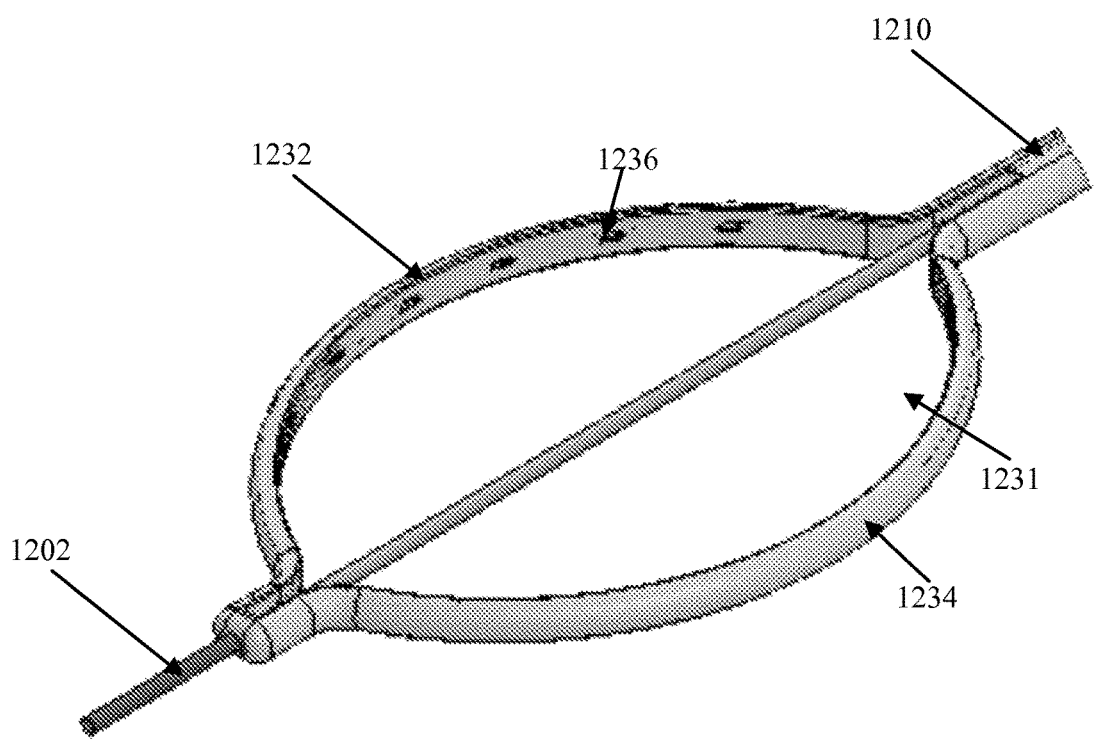
FIGS. 12A-C show views of a deliver device according to embodiments.
Figure 12B:
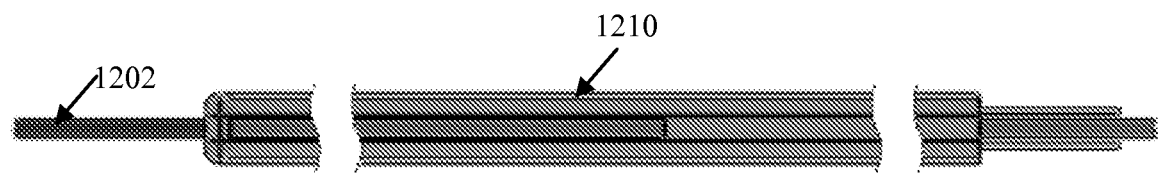
Figure 12C:
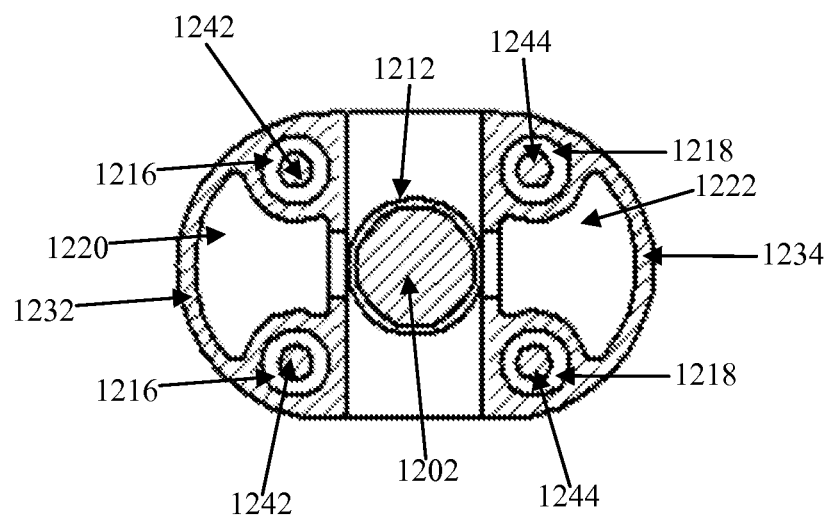
Figure 13A:
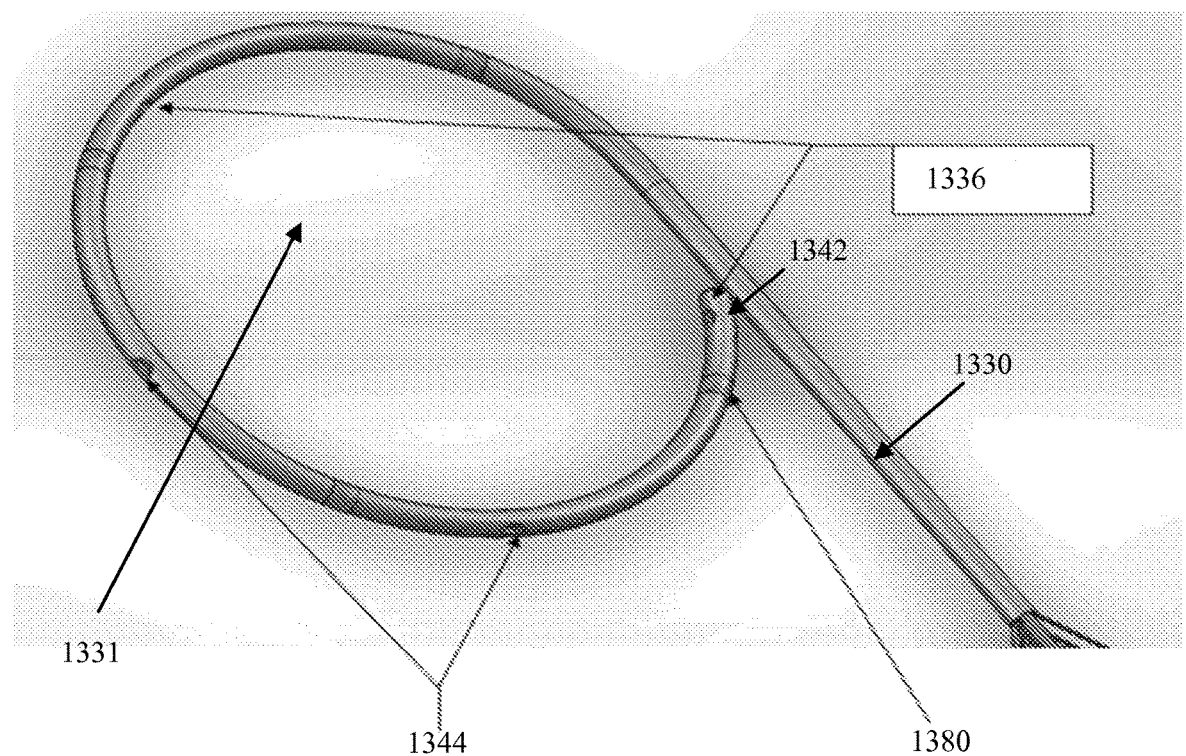
FIGS. 13A and 13B show views of a delivery device according to embodiments.
Figure 13B:
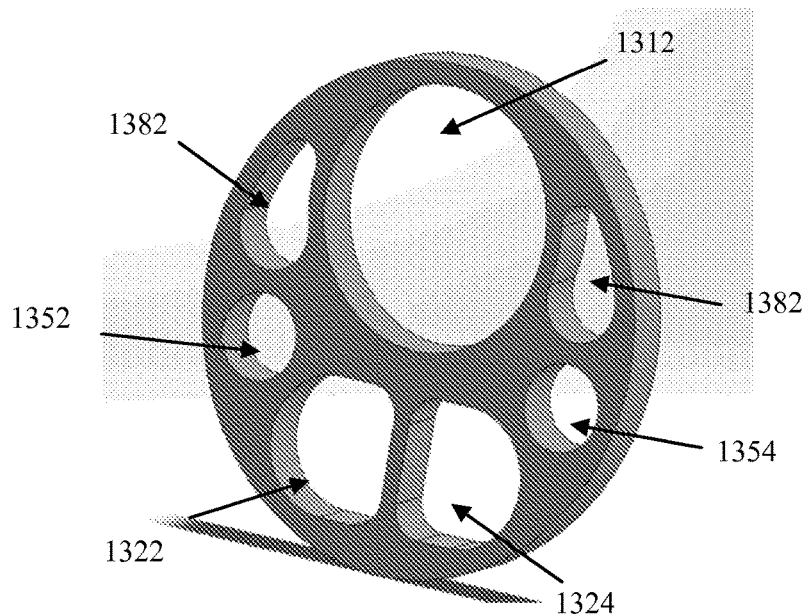

FIGS. 13A and 13B show a delivery device 1300 with a member configured to define a barrier region by a suction seal. Like the delivery device 200, the delivery device 1300 may include a member 1330 configured to advance and/or retract with respect to a body (not shown) and configured to define a barrier region 1331 in which one or more therapeutic materials may be delivered when the member 1330 is advanced, and the body (not shown). It will be understood that the body may correspond to embodiments, for example, the body described with respect to FIGS. 2-12 and 14-16.

In some embodiments, the member 1330 may be retractable with respect to a body (not shown) and configured to define the barrier region 1331 (e.g., in a closed state). In some embodiments, the member 1330 may be configured to curl upon itself so that a portion of the member 1330 overlaps with another portion of the member 1330, for example, as shown in FIGS. 14-16. In some embodiments, the member 1330 may include one or more ports 1342 disposed at an end of the member 1330 and/or along one or more surfaces of the member 1330. In some embodiments, the one or more ports 1342 may be configured to delivery suction so as to cause the member 1330 to seal the defined region by sealing upon itself.

In some embodiments, the member 1330 may include one or more ports 1344 configured to deliver suction so that the surrounding tissue temporarily adheres to the member 1330. In some embodiments, the member 1330 may include two sets of the one or more ports 1344 disposed on opposing surfaces of member 1330. In some embodiments, the member 1330 may include less or more sets of one or more ports 1344. By way of example, the member 1330 may include on one set of ports 1344 disposed on one surface of the member 1330. When the suction is applied, the one or more ports 1344 may cause the surrounding tissue to act as a roof for the defined region In some embodiments, the member 1330 may include a plurality of ports 1336 configured to deliver one or more therapeutic materials. In some embodiments, the ports 1336 may be any number, shape, pattern, size, or spacing. In some embodiments, the member 1330 may include two sets of the ports 1336 disposed at different positions on a surface of the member 1330. In some embodiments, each set of the ports 1336 may be configured to deliver a different therapeutic material. In some embodiments, the member 1330 may include more or less sets of ports. In some embodiments, each set of the ports 1336 may be configured to deliver the same therapeutic material. In some embodiments, the ports 1336 may be disposed at an angle.

In some embodiments, the sets of the ports 1336 may be disposed on a region or surface of the member 1330 between the sets of the ports 1344 configured to delivery suction. The ports 1336 may be disposed on the surface of the member 1330 so that in use the ports 1336 can be disposed in the internal surface of the defined region (e.g., when the member 1330 is in a closed state) so that the ports 1336 can deliver the therapeutic materials within the defined region. In some embodiments, the sets of ports 1344 can be disposed on opposing surfaces that are perpendicular to the surface of the ports 1336 so to surround region and/or face the surrounding tissue. In some embodiments, the ports 1342 may be disposed on the region or surface opposite of the ports 1336 so that in use, the ports 1342 can face a surface of the member 1330.

In some embodiments, the member 1330 may include a plurality of electrical sensors 1380 disposed along the length of the member. Each sensor 1380 may be disposed at least partially about the circumference of the member 1340.

In some embodiments, as shown in the cross-section in FIG. 13B, the member 1330 may include a plurality of lumens disposed along its length. In some embodiments, the member 1330 may include a lumen 1312 configured for a steering member (not shown) that can control the movement of the member 1330 in the formation of the region (e.g. so as to be in a closed state) with respect to a body. The other lumens may be arranged so as to surround the lumen 1312.

In some embodiments, the member 1330 may also include lumens 1322 and 1324 configured to deliver one or more therapeutic materials. For example, each lumen may deliver a different part of a two-part material. In some embodiments, the lumens 1322 and 1324 may be combined for delivering the same therapeutic material and/or different therapeutic materials. The lumens 1322 and 1324 may communicate with a set of the one or more ports 1336 to deliver the material within the defined region.

The member 1330 may include one or more lumens 1352 and 1354 configured to deliver suction to the surrounding tissue through the ports 1342 and/or 1344. In some embodiments, the suction may be provided for each lumen by the same vacuum source or independently provided. By way of example, the lumen 1352 may be for the set of ports 1342 configured to face the epicardial tissue and the lumen 1354 may be for the set of ports 1342 configured to face the pericardial tissue when the member 1330 is in use. The member 1330 and/or the body may include one or more lumens 1382 in which sensing wires may be disposed. The one or more lumens 1382 may be arranged so that the sensing wires communicate with the sensors 1380 disposed along the length of the member. The sensors 1380 may include any sensor, such as sensors configured to detect electrical activity in the heart.

FIGS. 14-16 show a delivery device including a member 1430 configured to curl within itself so that a portion of the member overlaps with another portion of the member and a body according to embodiments. FIGS. 14-16 show a body including one or more stabilizing members configured to stabilize the body with respect to the treatment site when the member 1430 is retracted from the overlapped or closed state. In this way, by stabilizing the body with respect to the treatment site, the member 1430 may be retracted without disrupting the delivered therapeutic material and prevent movement of the body that could be caused by the force of the retraction.

FIGS. 14-16 show a delivery device that includes body according to different embodiments. It will be understood that the delivery device is not limited to the configuration shown in the figures. By way of example, it will be understood that it may include a different member(s) and/or the member 1430 may be disposed within a different body.

As shown in FIGS. 14 A and B, the delivery device 1400 may include the member 1430 and a body 1410. In some embodiments, the delivery device 1430 may be advanced or deployed from the body 140 so that a section of the member 1430 curls until a portion of the member 1430 disposed at an end 1432 overlaps with another portion. For example, in use, the member 1430 can be advanced or deployed from so that a portion 1433 of the member 1430 (disposed adjacent to the end of the member 1430) is disposed adjacent to portion 1435 (disposed adjacent to the end of the member 1430).

In some embodiments, the member 1430 may include one or more sets of one or more ports 1444 configured to deliver suction so that the surrounding tissue at the treatment site temporarily adheres to the member 1430. In some embodiments, the member 1430 may include two sets of the one or more ports 1444 disposed on opposing surfaces of member 1430. In some embodiments, the member 1430 may include less or more sets of one or more ports 1444. By way of example, the member 1430 may include one set of ports 1444 disposed on one surface of the member 1430. When the suction is applied, the one or more ports 1444 may cause the surrounding tissue to act as a roof for the defined region In some embodiments, the member 1430 may include one or more sets of plurality of ports 1436 configured to deliver of one or more therapeutic materials. In some embodiments, the ports 1436 may be any number, shape, pattern, size, or spacing. In some embodiments, the member 1430 may include two sets of the ports 1437 and 1439 disposed at different positions on a surface of the member 1430. In some embodiments, each set of the ports 1436 may be configured to deliver a different therapeutic material. In some embodiments, the member 1430 may include more or less sets of ports. In some embodiments, each set of the ports 1436 may be configured to deliver the same therapeutic material. In some embodiments, the ports 1436 may be disposed at an angle.

In some embodiments, the sets of the ports 1436 may be disposed on a region or surface of the member 1430 between the sets of the ports 1444 configured to delivery suction. The ports 1436 may be disposed on the surface of the member 1430 so that in use the ports 1436 can be disposed in the internal surface of the defined region (e.g., when the member 1430 is in a closed state) so that the ports 1436 can deliver the therapeutic materials within the defined region. In some embodiments, the sets of ports 1444 can be disposed on opposing surfaces that are perpendicular to the surface of the ports 1436 so to surround region and/or face the surrounding tissue. In some embodiments, the ports 1444 may be disposed on the region or surface on the member opposite of the ports 1436 so that in use, the ports 1444 can face a surface of the member 1430 when overlapped.

In some embodiments, the member 1430 may include a plurality of electrical sensors 1480 disposed along the length of the member. Each sensor 1480 may be disposed at least partially about the circumference of the member 1440.

Figure 14A:
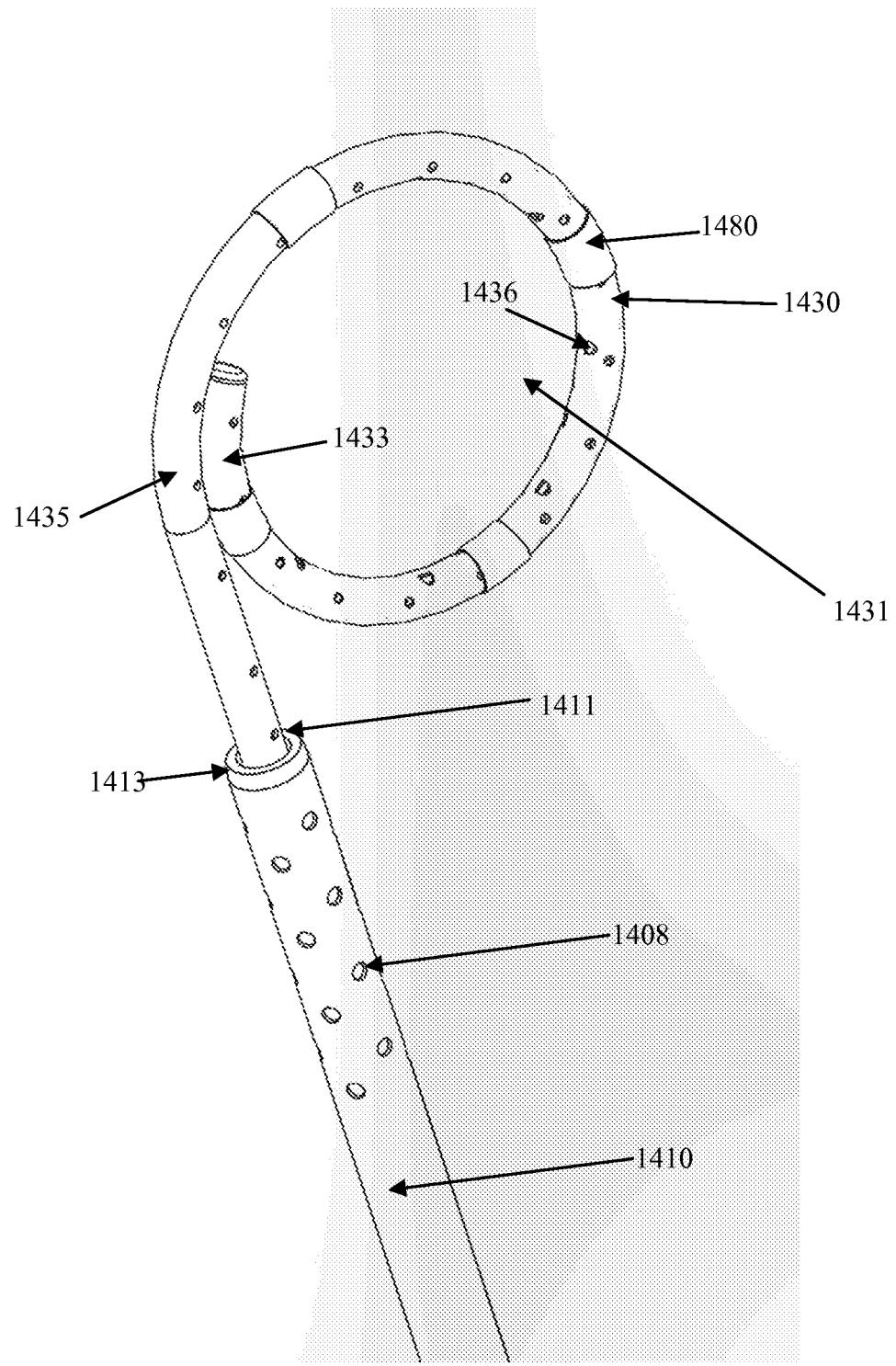
FIGS. 14A-D show views of a delivery device according to embodiments.

In FIGS. 14A and B, the member 1430 has a closed end. The end may be blunt, rounded, as well as other shapes. In some embodiments, the member 1430 may have a port disposed at the end, for example, to deliver one or more therapeutic materials.

Figure 14B:
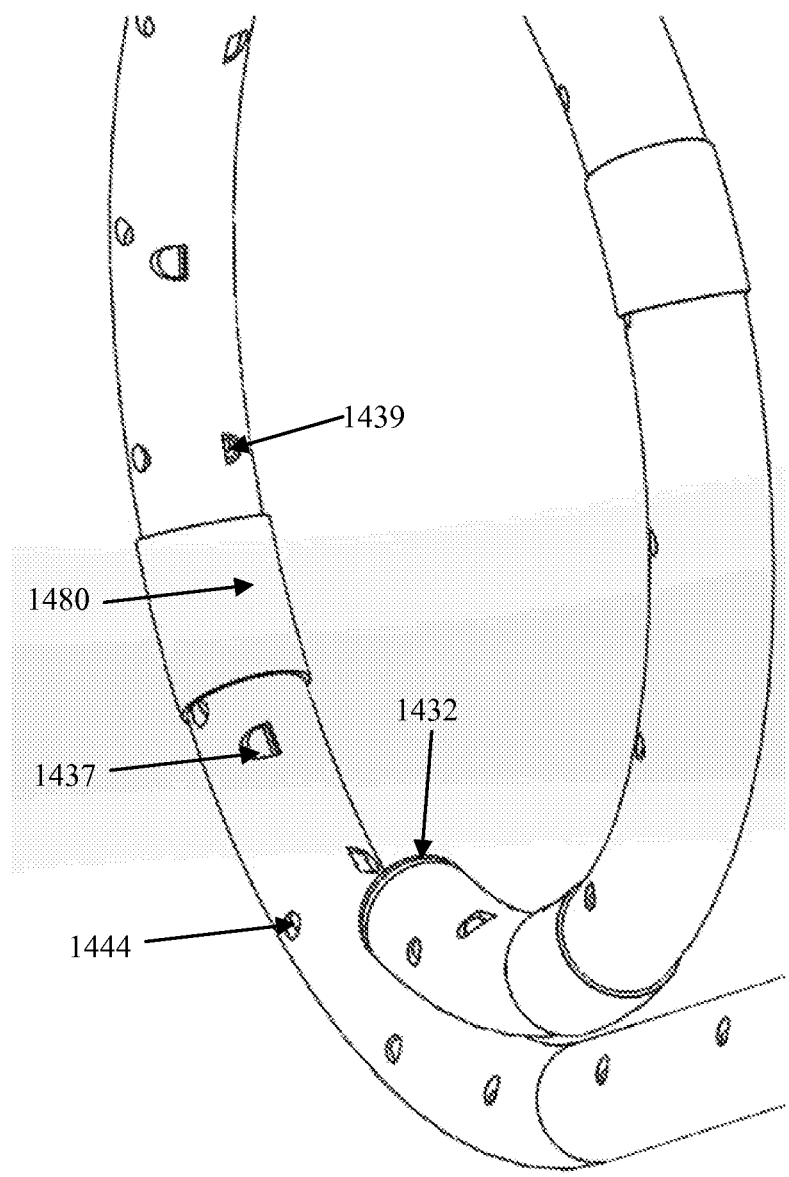
Figure 14C:
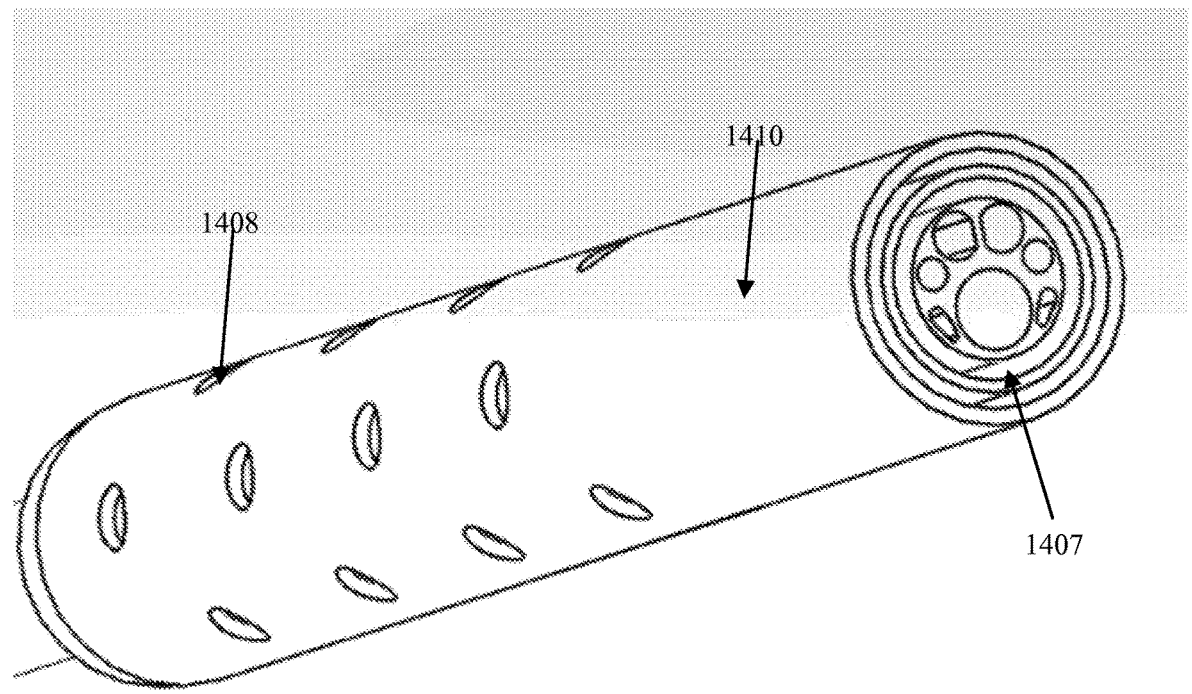
Figure 14D:
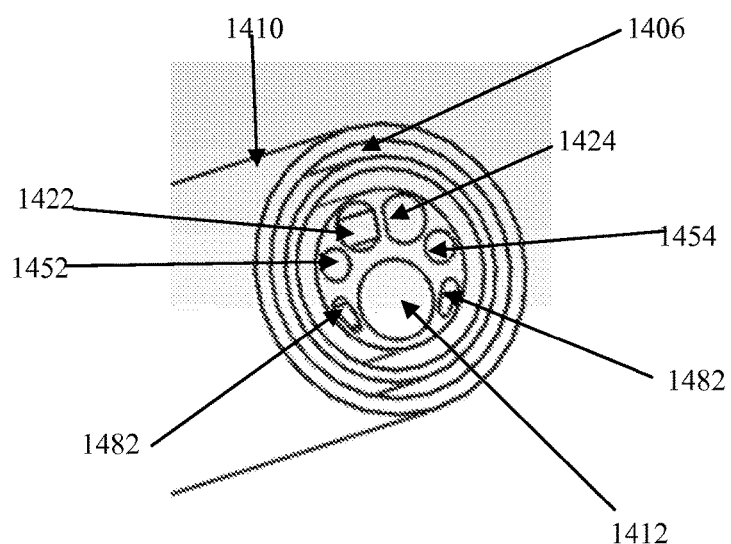

In some embodiments, as shown in the cross-section in FIGS. 14C and D, the member 1430 may include a plurality of lumens disposed at least partially along its length. In some embodiments, the member 1430 may include a lumen 1412 configured for a steering member (not shown) that can control the movement of the member 1430 in the formation of the region (e.g. so as to be in a closed state) with respect to a body. For example, the steering member may be configured to cause the member 1430 to overlap as shown in FIGS. 14A and 14B. The other lumens may be arranged so as to surround the lumen 1412.

In some embodiments, the member 1430 may also include lumens 1422 and 1424 configured to deliver one or more therapeutic materials. For example, each lumen may deliver a different part of a two-part material. In some embodiments, the lumens 1422 and 1424 may be combined for delivering the same therapeutic material and/or different therapeutic materials. The lumens 1422 and 1424 may communicate with ports sets 1437 and 1439, respectively, to deliver the material within the defined region.

In some embodiments, the member 1430 may include lumens 1452 and 1454. The lumens 1452 and 1454 may be configured to deliver suction to the surrounding tissue at least through the ports 1442. In some embodiments, the suction may be provided for each lumen by the same vacuum source or independently provided. By way of example, the lumen 1452 may be for the set of ports 1442 configured to face the epicardial tissue and the lumen 1454 may be for the set of ports 1442 configured to face the pericardial tissue when the member 1430 is in use.

In some embodiments, the member 1430 may include one or more lumens 1482 in which sensing wires or other component wires may be disposed. In some embodiments, the member 1430 may include two lumens 1482 configured for sensing wires. In some embodiments, the member 1430 may include more or less lumens. The one or more lumens 1482 may be arranged so that the sensing wires communicate with the sensors 1480 disposed along the length of the member. The sensors 1480 may include any sensor, such as sensors configured to detect electrical activity in the heart.

In some embodiments, the member 1430 may also include one or more ports disposed along the portions 1433 and/or 1435 of the member 1430. The one or more ports may communicate with the lumens 1452 and/or 1454. In some embodiments, the one or more ports may be configured to deliver suction so as to cause the member 1430 to seal the defined region by sealing upon itself. In some embodiments, the member 1430 may additionally or alternatively further include other connecting members disposed on the portions 1433 and/or 1435. In some embodiments, the connecting members may include but are not limited to complimentary magnets.

In some embodiments, the body 1410 may include a tapered tip 1411 disposed at the distal end 1413. The body 1410 may also include one or more stabilizing members 1408 disposed at least partially along the length of the body 1410 near the distal end and along the circumference of the body 1410. By way of example, the one or more stabilizing members 1408 may be one or more ports configured to deliver suction to the adjacent tissue at the treatment site. In some embodiments, the one or more stabilizing members 1408 may include a plurality of sets of one or more stabilizing members that are disposed offset with respect to the length of the body 1410. In some embodiments, each set of stabilizing members may include any number of stabilizing members and may be more or less than the four stabilizing members 1408 shown. In some embodiments, the plurality of stabilizing members 1408 may be aligned with respect to the length. In some embodiments, the one or more stabilizing members 1408 may another type of stabilizing member (e.g., retractable spike, other protruding element, clamp, hook, etc.).

As shown in FIGS. 14C and D, the body 1410 may include at least one lumen 1406 that is adjacent to the lumen 1407. The lumen 1407 may be configured for the member 1430. The member 1430 may be configured to move (advance and/or retract) with respect to the body through the lumen 1407. In some embodiments, the lumen 1406 may be configured to surround the lumen 1407. In some embodiments, the lumen 1406 may be configured to activate the stabilizing members 1408. For example, the lumen 1406 may be configured to deliver suction from a vacuum source through the stabilizing members 1408 to the surrounding tissue at the treatment site. In some embodiments, the lumen 1406 may be compartmentalized and/or integrated for each set of members 1408.

In use, the member 1430 may be advanced through the lumen 1407 of the body 1430 using a steering member disposed in the lumen 1412. In some embodiments, the member 1430 may be advanced past the body into the treatment site so that the portions 1433 and 1435 are caused to be adjacent to each other (overlap) to define the region 1431 as shown in FIGS. 14A and B. After the barrier region is form, the suction may be applied through ports 1442 so that the surrounding tissue (e.g., epicardial and pericardial tissue) may also temporarily adhere to the respective surfaces of the member and thereby the tissues can act as a roof for the barrier region 1431. In this way, the region 1431 may be substantially sealed. After the region 1431 is sealed, one or more therapeutic materials may be delivered into the barrier region 1431 defined by the member 1430 using the ports 1436. In some embodiments, a different therapeutic material may be delivered through each set of ports through the respective lumen in the member 1430. The members 1430 may be remain within the target site until the one or more therapeutic materials, for example, engraft and/or gelate. After which, the suction delivered through the ports 1442 of the member 1430 may be stopped and the suction may then be delivered through the ports 1408 through the lumen 1407 of the body 1410 to stabilize the body 1410 with respect to the treatment site. After the body 1410 is stabilized, the member 1430 may be unfurled from around the material(s) 1470 without disturbing the material and retracted back into the body (not shown), for example, using the steering member (not shown) via the lumen 1412. By way of example, the steering member and/or the member 1430 may be made of a shape memory alloy with a predefined shape that may allow formation of the barrier region by the member 1430 and the retraction of the member 1430 without disturbing the delivered material.

In some embodiments, the body may have a different configuration of the stabilizing members. FIGS. 15 and 16 show examples of delivery devices with different bodies according to embodiments. It will be understood that the body may have a different configuration. By way of example, the body may include any number of lumens, any number of sets of stabilizing members, any shape, any size, any pattern, any stabilizing members, among others, or a combination thereof.

Figure 15A:
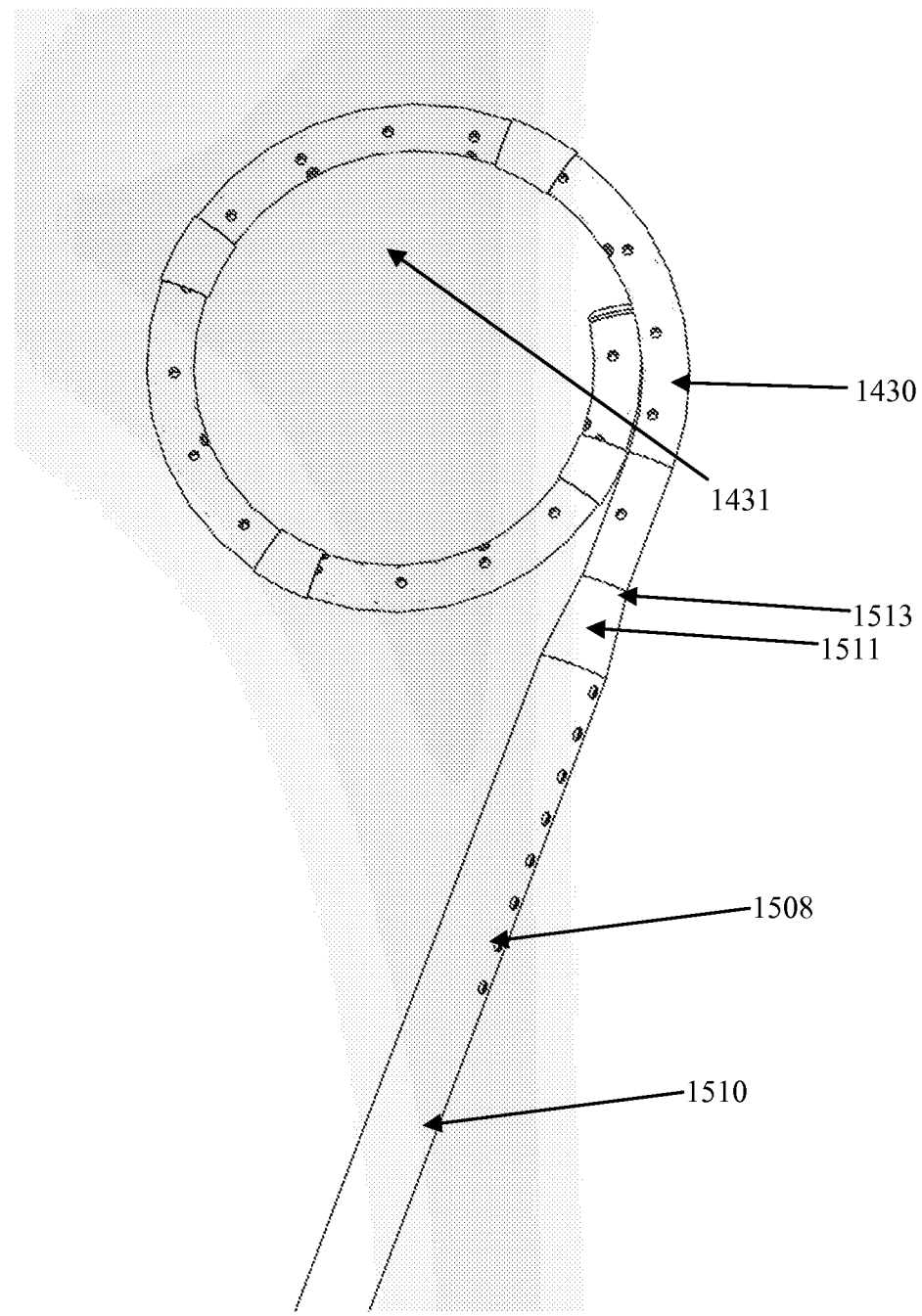
FIGS. 15 A and B show view of a delivery device according to embodiments.

FIGS. 15A and B show a delivery device 1500 that includes a body 1510 and the member 1430 according to embodiments. In some embodiments, the body 1510 may include a tapered tip 1511 disposed at the distal end 1513. The body 1510 may also include one or more stabilizing members 1508 disposed at least partially along the length of the body 1510 near the distal end 1513. By way of example, the one or more stabilizing members 1508 may include one or more ports configured to deliver suction to the adjacent tissue at the treatment site. In some embodiments, the one or more stabilizing members 1508 may include a plurality of sets of one or more stabilizing members that are spaced in a row partially along the length of the body 1510. In some embodiments, each set of stabilizing members may include any number of stabilizing members and may be more or less than the stabilizing members 1508 shown. In some embodiments, the one or more stabilizing members 1508 may another type of stabilizing member (e.g., retractable spike, other protruding element, etc.).

Figure 15B:
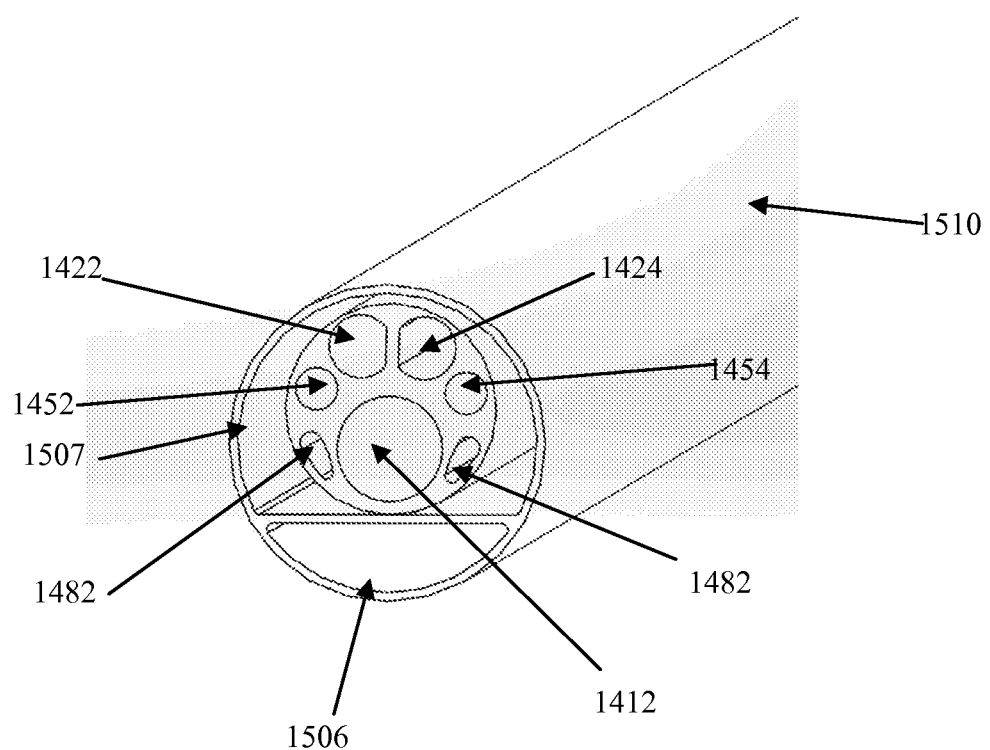

As shown in FIGS. 15A and 15B, the body 1510 may include at least one lumen 1506 that is adjacent to the lumen 1507. The lumen 1507 may be configured for the member 1430. The member 1530 may be configured to move (advance and/or retract) with respect to the body through the lumen 1507. In some embodiments, the body 1510 may be divided into the lumen 1506 and the lumen 1507. In some embodiments, the lumen 1506 may be configured to activate the stabilizing members 1508. For example, the lumen 1506 may be configured to deliver suction from a vacuum source through the stabilizing members 1508 to the surrounding tissue at the treatment site. In some embodiments, the lumen 1506 may be compartmentalized and/or integrated for each set of members 1508. In use, the device 1500 may be operated the same as the device 1400 by using the lumens 1506 and 1507.

Figure 16A:
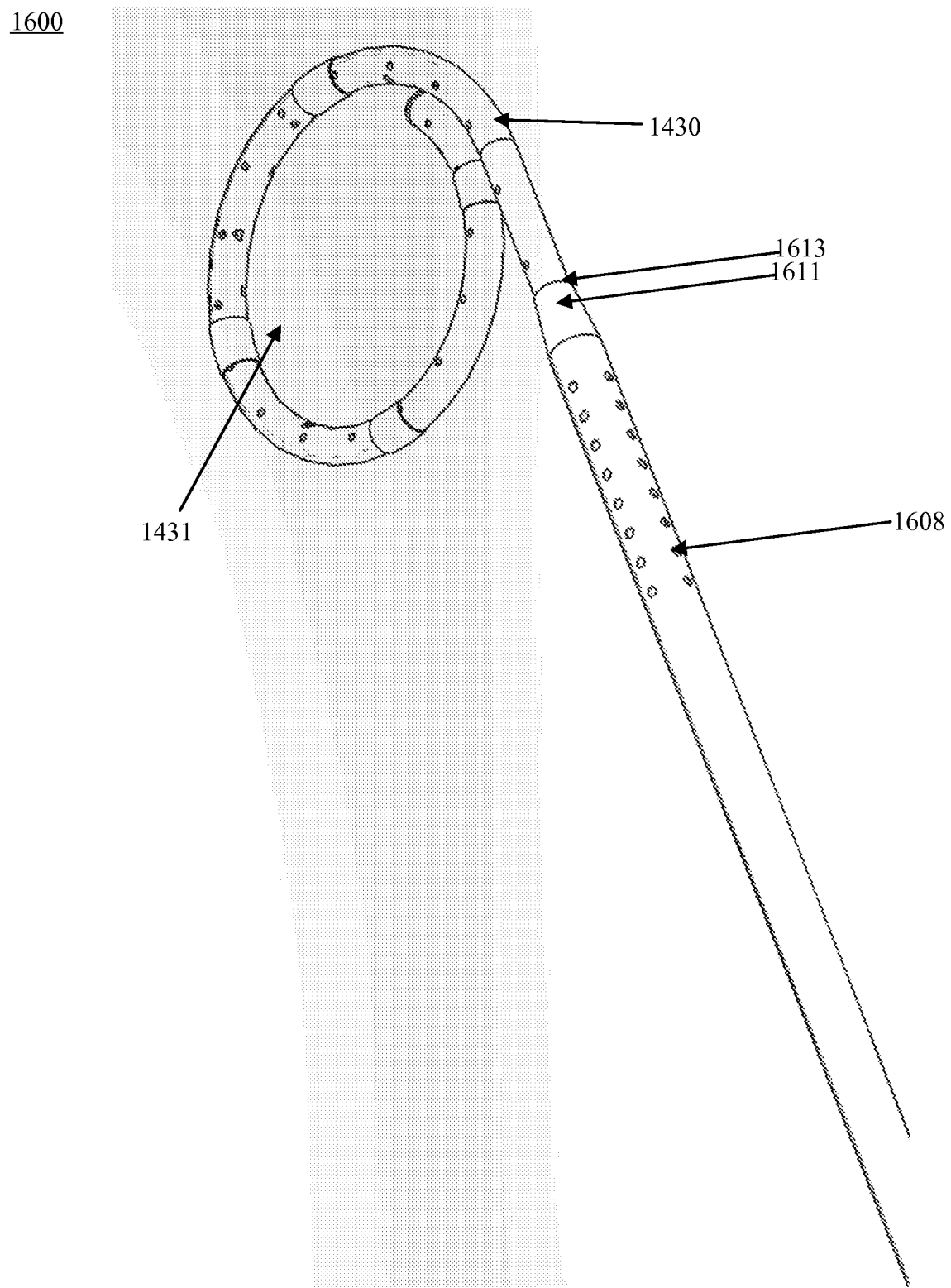
FIGS. 16A and B show views of a delivery device according to embodiments.

FIGS. 16A and B show a delivery device 1600 that includes a body 1610 and the member 1430 according to embodiments. In some embodiments, the body 1610 may include a tapered tip 1611 disposed at the distal end 1613. The body 1610 may also include one or more stabilizing members 1608 disposed at least partially along the length of the body 1610 near the distal end. By way of example, the one or more stabilizing members 1608 may be one or more ports configured to deliver suction to the adjacent tissue at the treatment site. In some embodiments, the one or more stabilizing members 1608 may include a plurality of sets of eight stabilizing members that are aligned with respect to the length of the body 1610. In some embodiments, the stabilizing members 1608 may include four sets of stabilized members that are aligned along the length of the body 1610 and evenly spaced around the circumference. The plurality of sets may include more or less than the number of the stabilizing members shown. In some embodiments, the stabilizing members may include any number of stabilizing members 1608 and may be more or less than the stabilizing members 1608 shown. In some embodiments, the one or more stabilizing members 1608 may another type of stabilizing member (e.g., retractable spike, other protruding element, etc.).

Figure 16B:
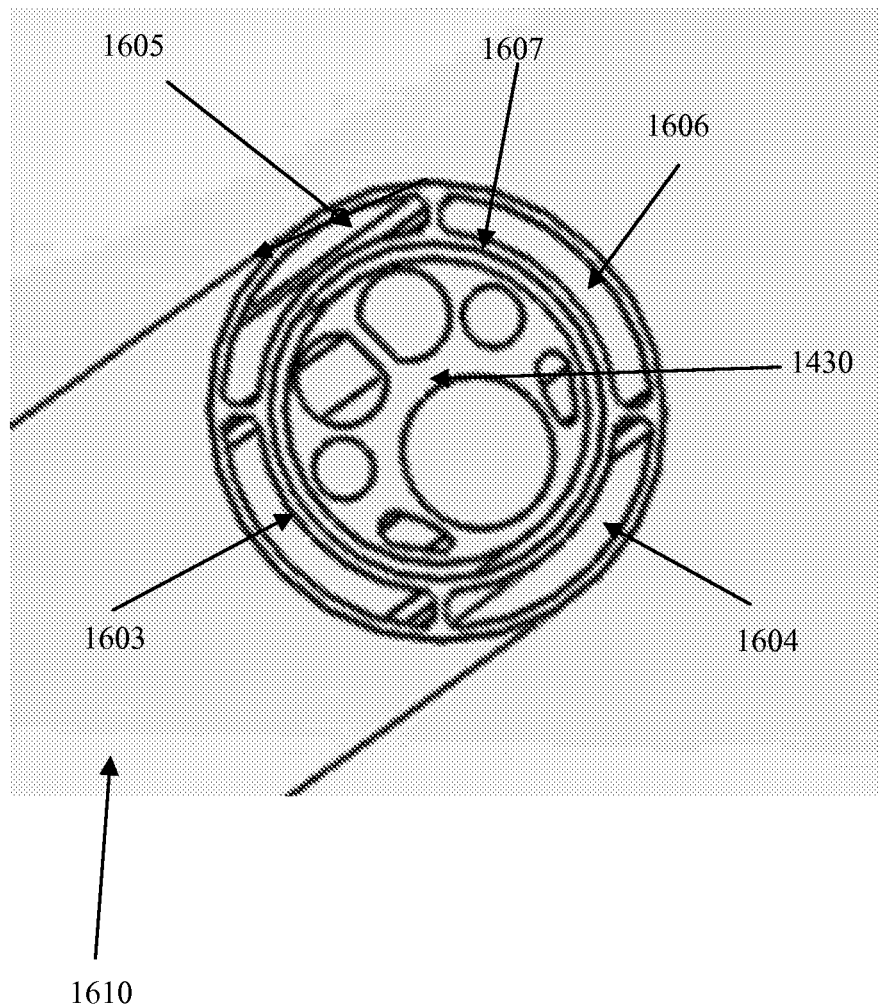

As shown in FIGS. 16A and 16B, the body 1610 may include a plurality of lumens that are adjacent to the lumen 1607. The lumen 1607 may be configured for the member 1430. The member 1630 may be configured to move (advance and/or retract) with respect to the body through the lumen 1607. The plurality of lumens may be disposed to surround the lumen 1607. In some embodiments, the plurality of lumens may include four lumens 1603-1606. For example, the lumen 1406 shown in FIG. 14 may be separated into a plurality of lumens, each lumen communicating with a set of ports. In the example shown in FIG. 16, each lumen 1603-1606 may communicate with each set (e.g., row) of the ports 1608. In some embodiments, the body 1610 may include more or less number of lumens. In some embodiments, the lumens 1603-1606 may be configured to activate the stabilizing members 1608. For example, the lumen 1603-1606 may be configured to deliver suction from a vacuum source through each set of the stabilizing members 1608 to the surrounding tissue at the treatment site. In use, the device 1600 may be operated the same as the device 1400 by using the lumens 1603-1606 and 1607.

Figure 17:
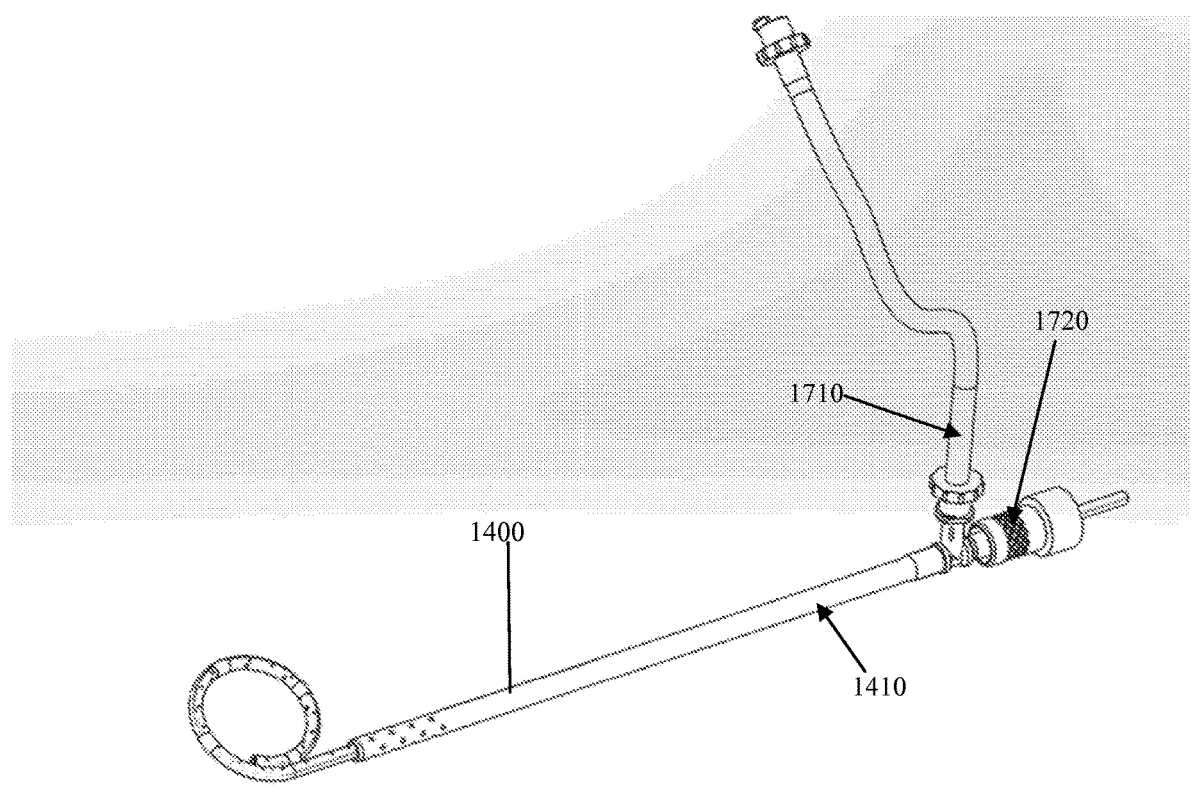
FIG. 17 shows a delivery system according to embodiments.

FIG. 17 shows an example of a delivery system 1700 for a delivery device according to embodiments. In some embodiments, the delivery system 1700 may include the delivery device 1400. In some embodiments, the delivery system 1700 may include a line 1710 that is attached to the body 1410 and is configured to communicate with a vacuum source. The line 1710, for example, may communicate with the lumen 1408 of the body 1410 to deliver the suction. In some embodiments, the system 1700 may include a separate line for the lumens 1452 and/or 1454 of the member 1430 to deliver the suction and/or the line 1710 may be configured to communicate with the member 1430. The system 1700 may also include a hemostatic seal 1720 attached to the body 1410 and configured to deliver the device 1400 to the treatment site.

It will be understood that the delivery system 1700 is not limited to the delivery device 1400. The delivery system 1700 may be used with other delivery devices according to embodiments. For example, the delivery system 1700 may include the delivery devices 1500 and/or 1600.

FIGS. 7-12 show a delivery device having two members configured to magnetically connect to define a barrier region in which one or more therapeutic materials may be delivered according to embodiments. FIGS. 7A-7D show a delivery device 700 including two members 732 and 734 configured to define a barrier region 731 in which one or more therapeutic materials may be delivered by magnetically connecting to each other. The device 700 may include a body 710.

In some embodiments, the members 732 and 734 may be controllable collectively and/or individually. The members 732 and 734 may be configured to be deployable and retractable with respect to the body 710 and configured to define the circular region 731 when deployed with respect to the body 710 into the treatment site. In some embodiments, each of the members 732 and 734 may include lumens 716 and 718, respectively and have at least one open end. In some embodiments, the device 700 may include one or more steering members 740 and 750 disposed within the lumens 716 and 718, respectively, configured to control the movement of the members 732 and 734, respectively, in the formation of the region 731. In some embodiments, the steering members 740 and 750 may be configured to move with and/or with respect to the respective members 732 and 734 within the respective lumens 716 and 718.

Figure 7A:
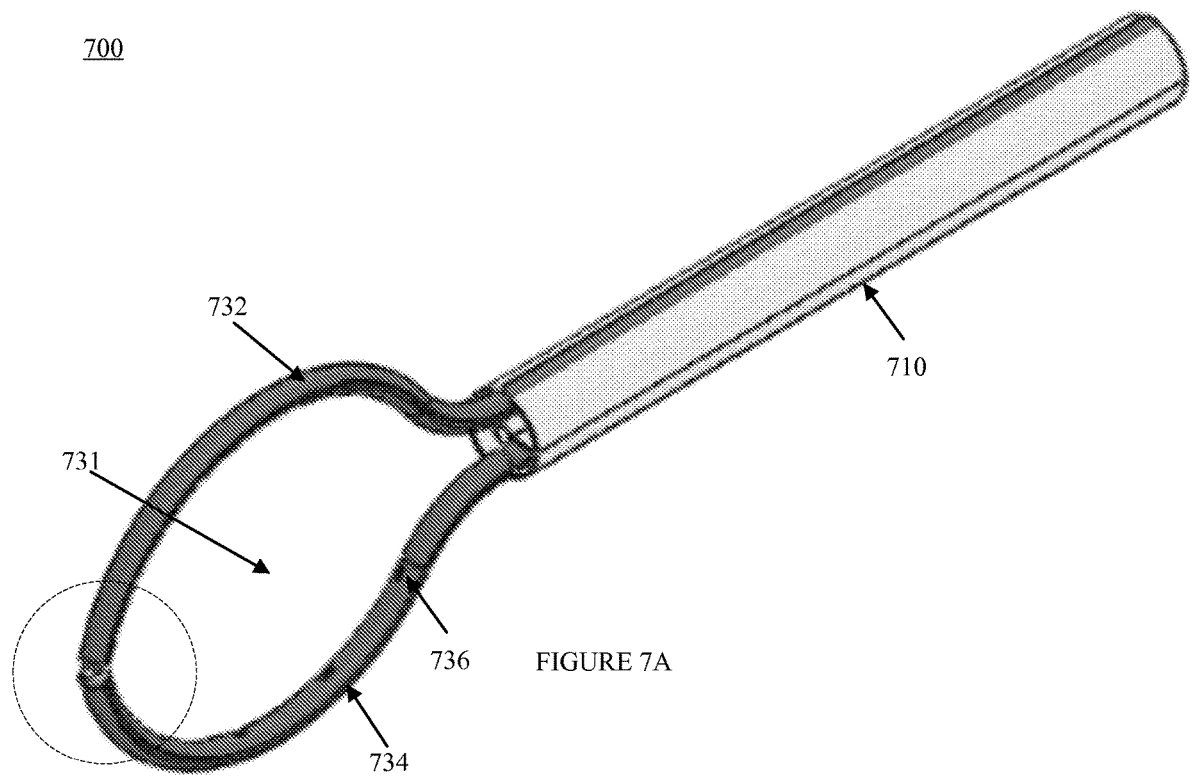
FIGS. 7A-D show views of a delivery device according to embodiments.
Figure 7B:
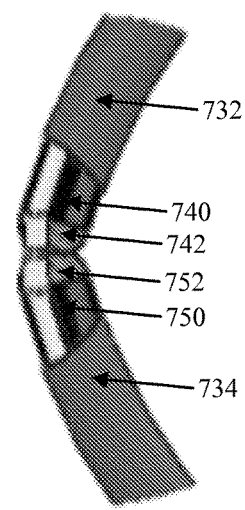
Figure 7C:
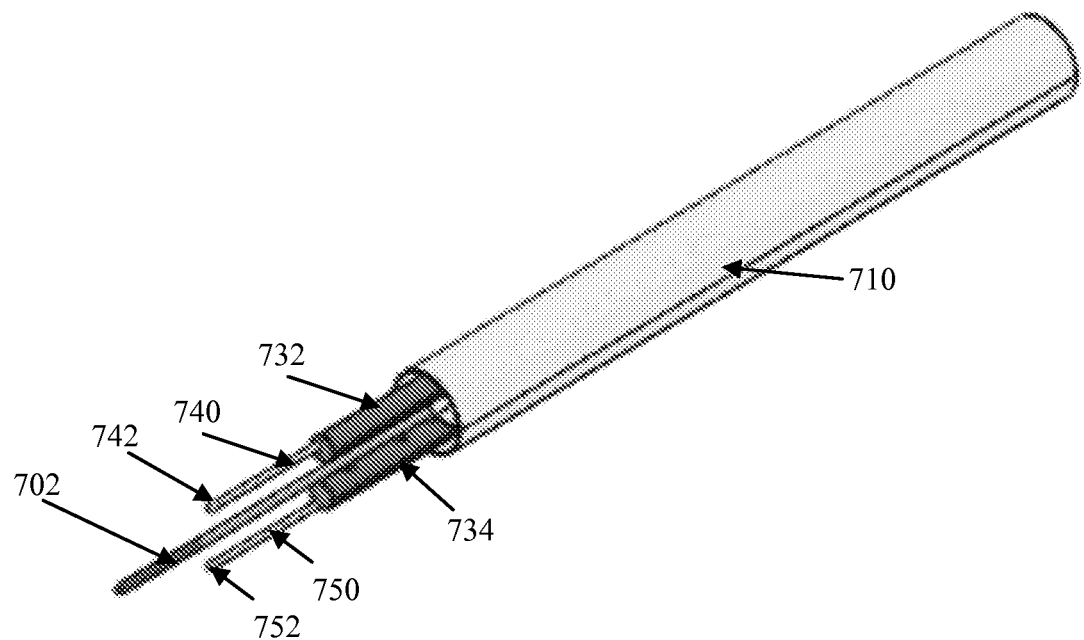

In some embodiments, each of the steering members 740 and 750 may include connecting members 742 and 744 disposed at the end, as shown in enlarged view in FIG. 7B. In some embodiments, the connecting members 742 and 744 may be complimentary. In some embodiments, the connecting members 742 and 744 may be magnets of opposite polarity so that they form a magnetic connection.

In some embodiments, the members 732 and 734 may be configured to connect to each other at about the apex of the defined region 731. In other embodiments, the members 732 and 734 may be configured to connect to each other at other points.

In some embodiments, the members 732 and 734 may each include a plurality of ports 736 disposed along the length configured to deliver one or more therapeutic materials.

Figure 7D:
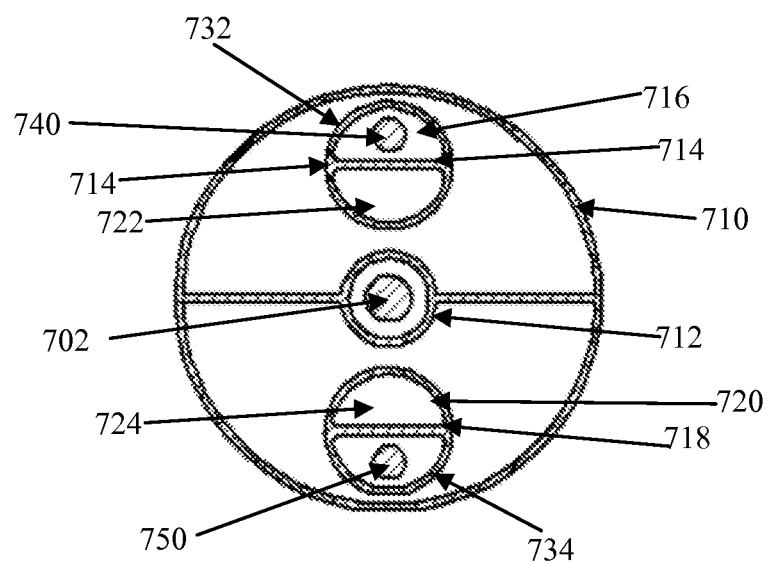

In some embodiments, as shown in the cross-section in FIG. 7D, the body 710 may include a plurality of lumens. In some embodiments, the body 710 may include a lumen 712 disposed in substantially the center of the body 710 configured for a guide wire 702. In some embodiments, the body may include lumens 714 and 718 configured for the members 732 and 734, respectively. In some embodiments, the members 732 and 734 may also include one or more lumens for delivering one or more therapeutic materials. In some embodiments, the members 732 and 734 may include lumens 722 and 724, respectively, for delivering the same therapeutic material and/or different therapeutic materials.

FIGS. 8A-8D show operation of members 832 and 834 similar to the device 700 shown in FIGS. 7A-7D. Like the device 700, each of the members 832 and 834 may include a lumen for steering members 840 and 850. In some embodiments, each of the steering members 740 and 850 may include a connecting member 842 and 852, respectively, disposed at the end. The connecting members 842 and 852 may have complementary magnetic polarity. In some embodiments, each of the members 832 and 834 may include a plurality of ports 836 to deliver one or more therapeutic materials and radiopaque tips 833 and 835, respectively, disposed at the ends. In some embodiments, the members 832 and 834 may be configured to fold or curl while disposed inside the body to assume a smaller shape, then enlarge or unfurl when outside of the device body.

Figure 8A:
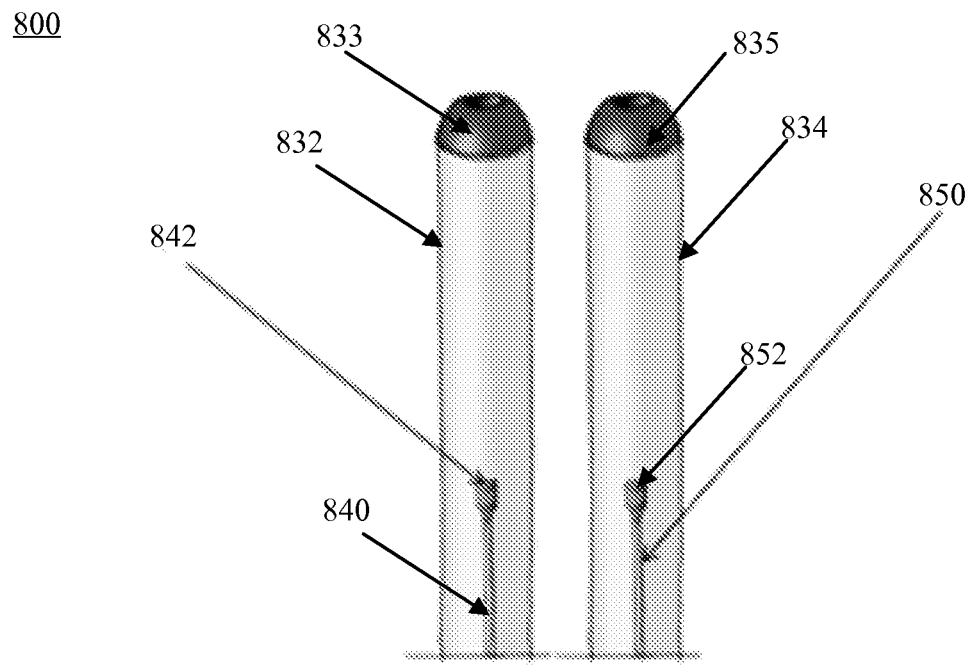
FIGS. 8A-E show operation of a delivery device according to embodiments.
Figure 8B:
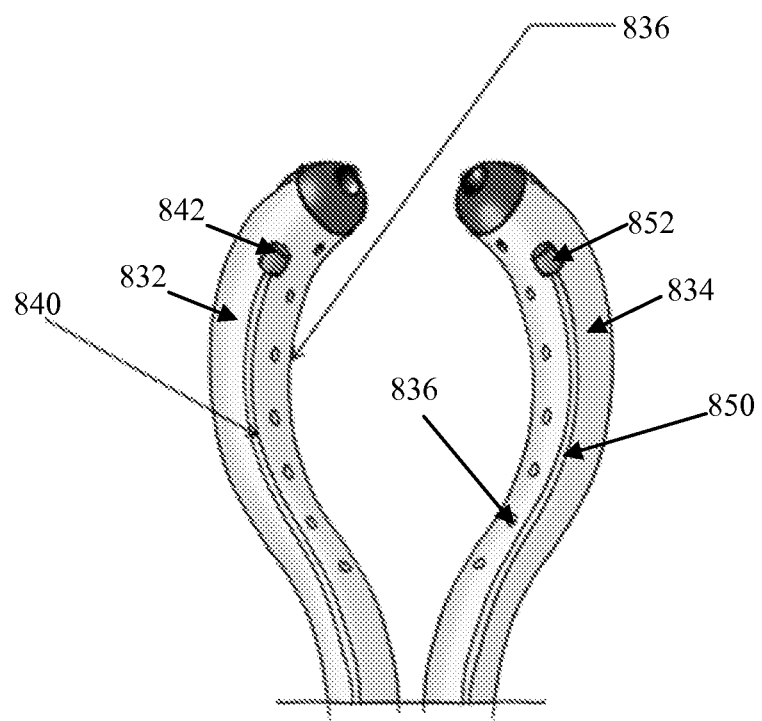
Figure 8C:
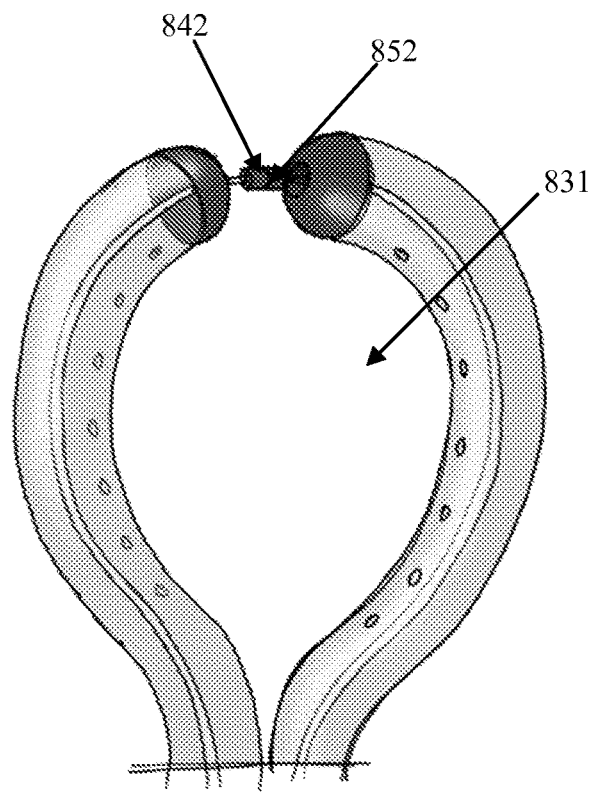
Figure 8D:
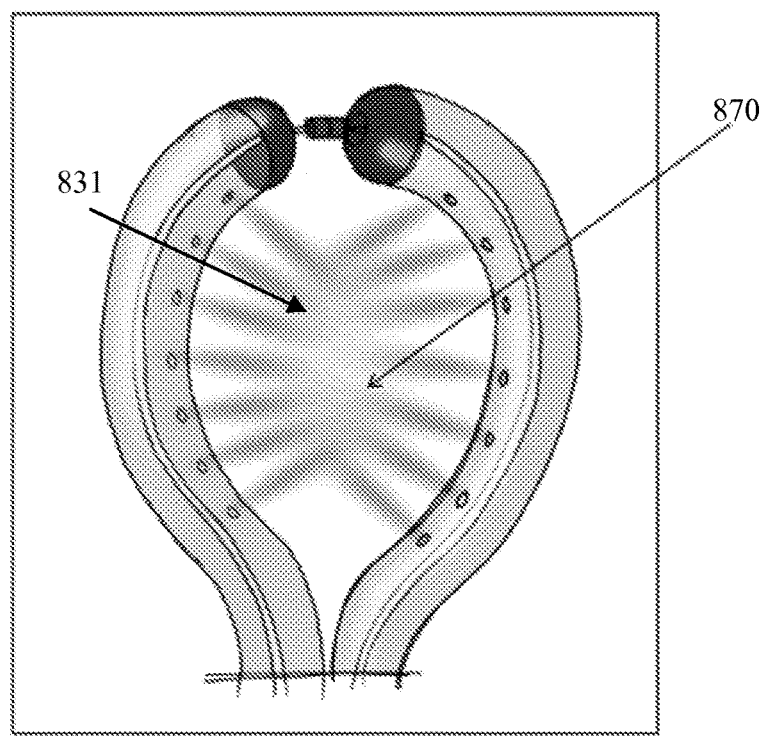
Figure 8E:
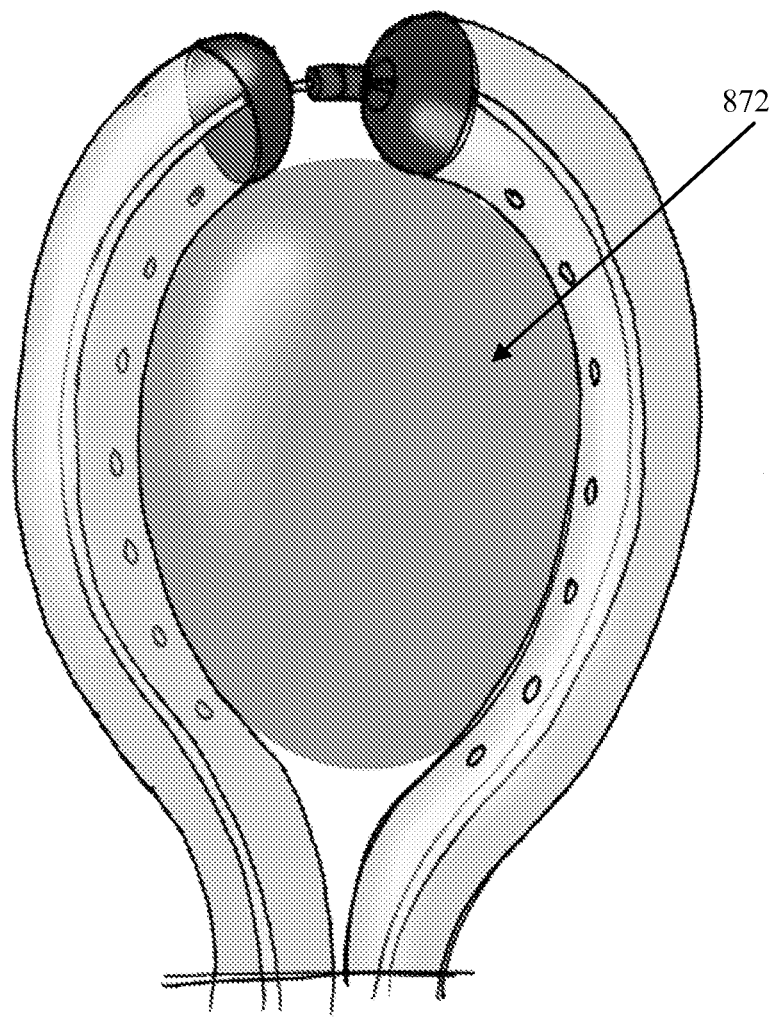

In operation, the steering members 840 and 850 may be advance or deployed through a body (not shown) and the respective members 832 and 834 to cause the members 832 and 834 to curve as shown FIG. 8B. The steering members 840 and 850 may be made of a shape memory material so as to cause the members 832 and 834 to form a pre-defined shape and region 831. After the connecting members 842 and 852 magnetically connect to define the region 831 shown in FIG. 8C, one or more therapeutic materials 870 may be delivered into the region 831 as shown in FIG. 8D. The members 832 and 834 may be remain within the target site until one or more therapeutic materials 870, for example, engraft and/or gelate, as shown in FIG. 8D. After which, the members 832 and 834 may be unfurled from around the material(s) 870 and retracted back into the body (not shown).

FIGS. 9A-9F show a delivery device 900 including two members 930 and 934 configured to define a barrier region 931 by mechanically connecting to each other. The device 900 may include a body 910. In some embodiments, the body 910 may include a tapered tip 911.

In some embodiments, the members 930 and 940 may be controllable collectively and/or individually. In some embodiments, the members 930 and 940 may be retractable with respect to the body 910 and configured to define the circular region 931. In other embodiments, one of the members 930 and 940 may be fixedly disposed with respect to the body 910.

In some embodiments, each of the members 930 and 940 may include connecting members 932 and 942 disposed at the end. In some embodiments, the connecting members 932 and 942 may be complimentary. In some embodiments, the connecting members 932 and 942 may be a hook and eye, respectively. In other embodiments, other mechanical connecting members may be used. In some embodiments, the body 910 may include a delivery lumen 912 configured to deliver one or more therapeutic materials 970.

In some embodiments, the members 930 and 940 may be configured to connect to each other at a position near and/or within the body 910. In other embodiments, the members 930 and 940 may be configured to connect to each other at other points. In some embodiments, the member 940 may be or deployed through the body 910 in a connected state with the member 930. In some embodiments, the advancement of the member 940 (without moving the member 930) may cause the member 940 to advance through the body in a connected state and to define the region 931.

Figure 9A:
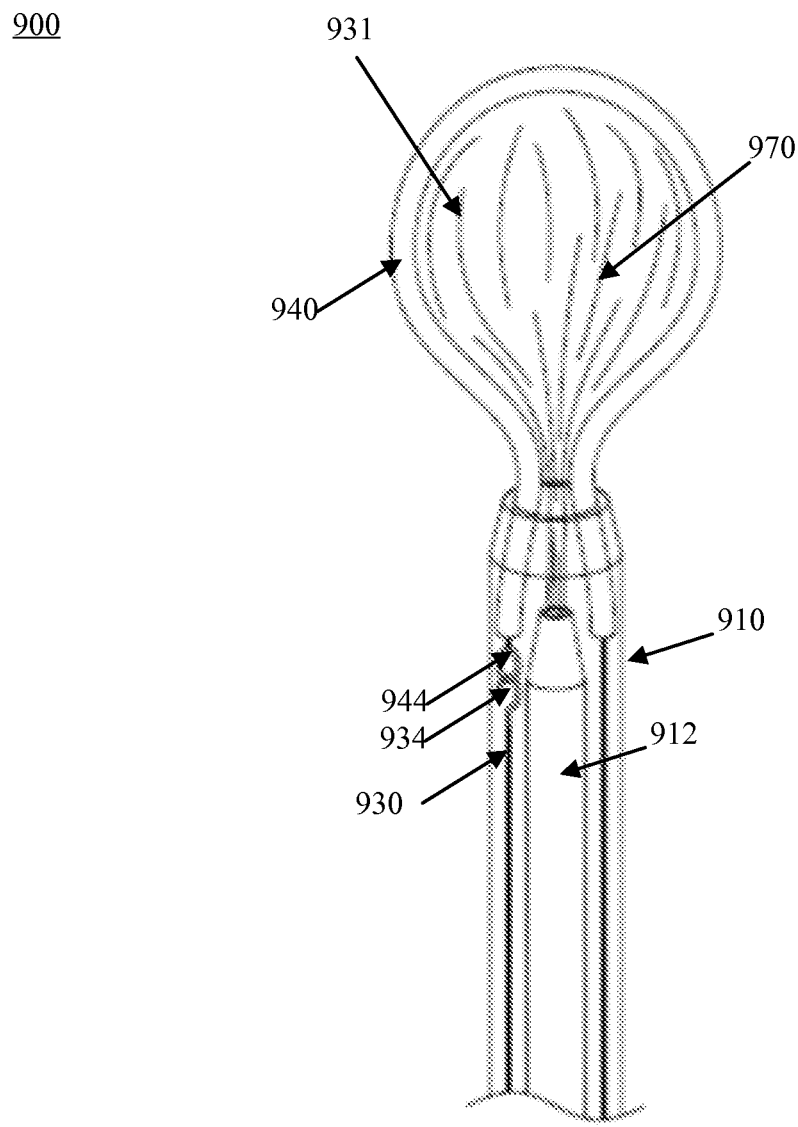

In operation, after the one or more therapeutic materials 970, for example, engraft and/or gelate, as shown in FIG. 9A, the member 940 may be unfurled from around the material(s) 970 and retracted back into the body 910, as shown in FIG. 9B-9E. As shown in these figures, the member 940 may be released from the connecting member 932, unfurled from the material 970, and retracted back into the body 910. In some embodiments, the member 930 may also be further retracted into the body 910. In other embodiments, the position of the member 930 may not change with respect the body 910.

Figure 10A:
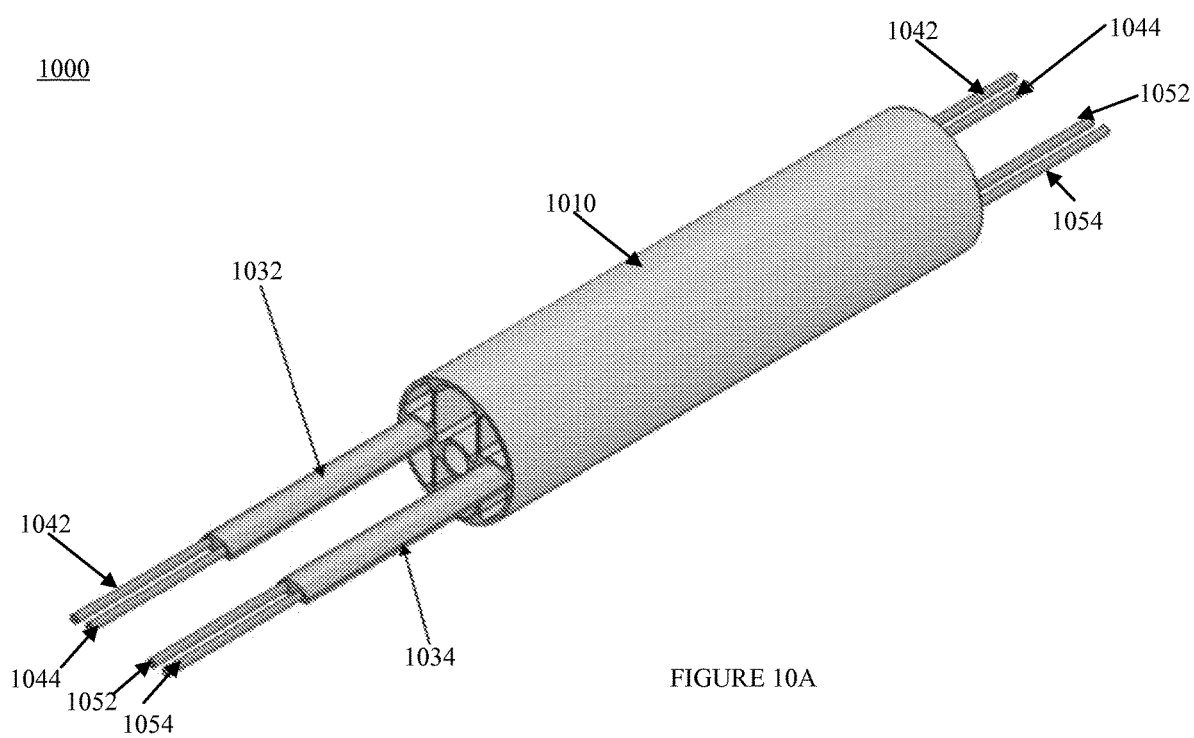
FIGS. 10A and 10B show views a delivery device according to embodiments.
Figure 10B:
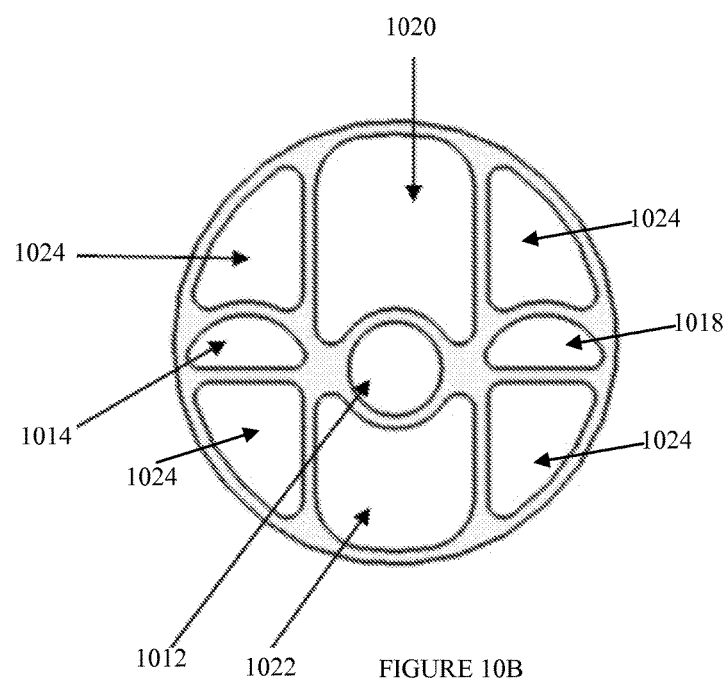

FIGS. 10A and 10B show a delivery device 1000 including two member 1032 and 1032 each having two connection members configured to magnetically connect to each other to define a barrier region in which one or more therapeutic materials may be delivered.

In some embodiments, the device 1000 may include a body 1010. Each of the members 1032 and 1034 may each include two lumens each for steering members 1042 and 1044, and steering members 1052 and 1054, respectively. In some embodiments, the steering members 1042 and 1044, and the steering members 1052 and 1054 may be configured to control the movement of the members 1032 and 1034, respectively, in the formation of a barrier region. In some embodiments, the steering members 1042 and 1044, and steering members 1052 and 1054 may be configured to move with and/or with respect to the respective members 1032 and 1034 within the respective lumens. By having additional steering members, the steering capabilities of the members may be enhanced. For example, the additional steering members may result more controlled unfurling of the members after the therapeutic material(s) are delivered and engrafted and/or gelated, and thereby may minimize interference with the engrafted and/or gelated therapeutic material(s).

In some embodiments, the members 1032 and 1034 may be controllable collectively and/or individually. The members 1032 and 1034 may be retractable with respect to the body 1010 and configured to define a barrier region.

In some embodiments, each of the steering members 1042 and 1044, and the steering members 1052 and 1054 may include a connecting members disposed at an end. In some embodiments, the connecting members may be complimentary. In some embodiments, the connecting members of the steering members 1042 and 1052 and the connecting members of the steering members 1044 and 1054 may be magnets of opposite polarity so that they form a magnetic connection.

In some embodiments, the members 1032 and 1034 may be configured to connect to each other at about the apex of the defined region. In other embodiments, the members 1032 and 1034 may be configured to connect to each other at other points.

In some embodiments, as shown in the cross-section in FIG. 10B, the body 1010 may include a plurality of lumens. In some embodiments, the body 1010 may include a lumen 1012 disposed in substantially the center of the body 1010 configured for a guide wire. In some embodiments, the body 1010 may include lumens 1014 and 1018 configured for the members 1032 and 1034, respectively. In some embodiments, the body 1010 may include two delivery lumens 1020 and 1022 configured for delivering the same therapeutic material and/or different therapeutic materials. In some embodiments, the body 1010 may also include one or more lumens 1024 for sensors. For example, the one or more lumens 1024 may be for sensors for detecting electrical activity in the heart.

Figure 11A:
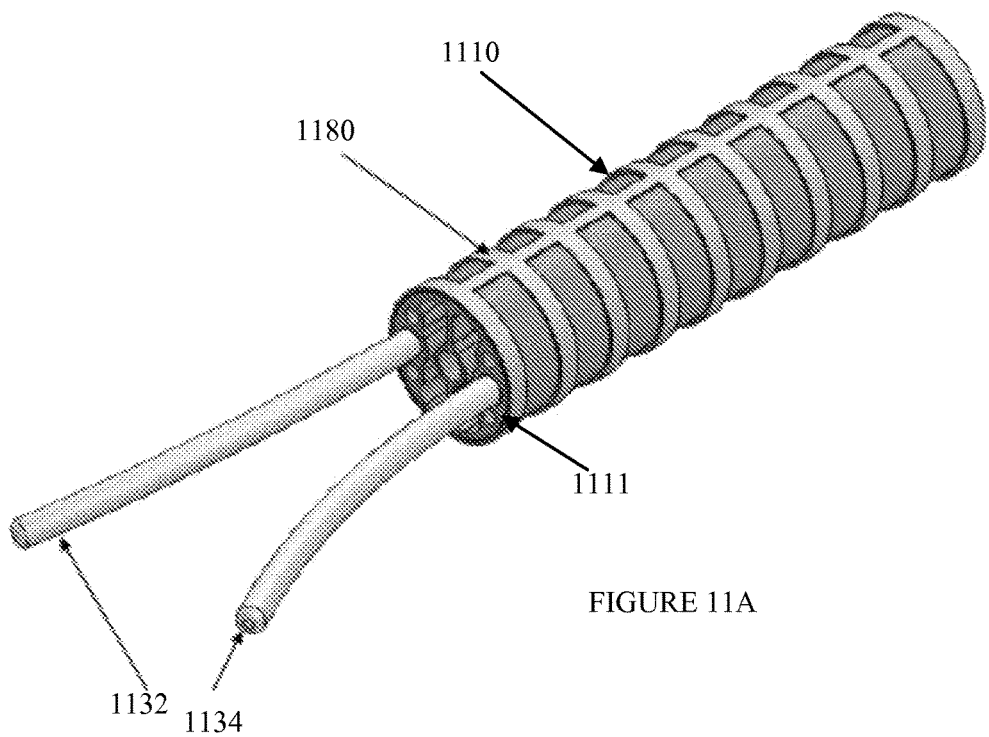
FIGS. 11A and 11B show views of a delivery device according to embodiments.
Figure 11B:
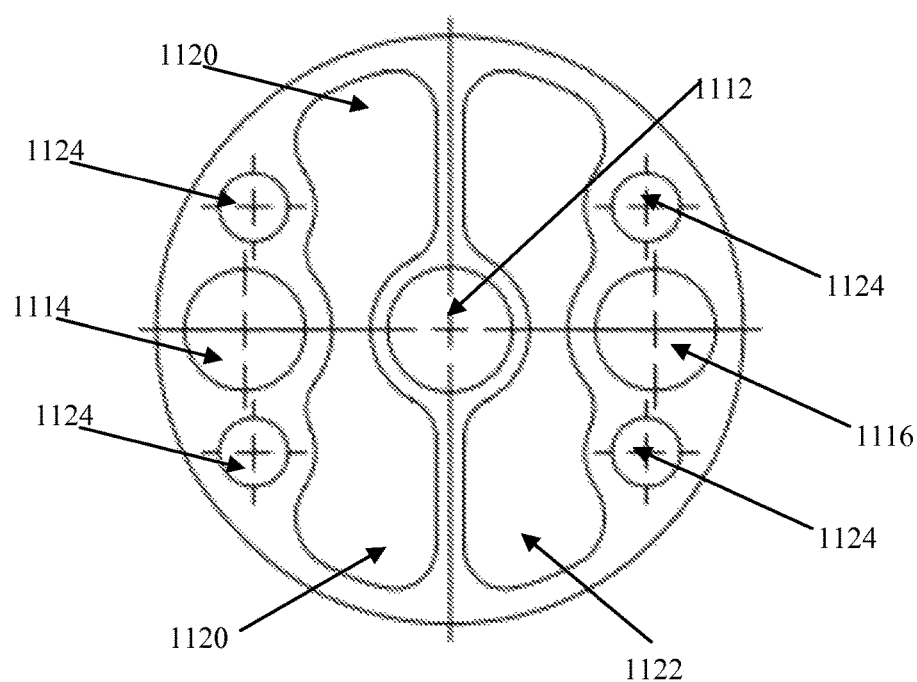

FIGS. 11A and 11B show a delivery device 1100 having a body 1110 that is configured to be self-folding. For example, the end 1111 may be configured to deform to form a barrier region with a specific radius of curvature. As shown in FIG. 11A, the body 1110 may include a plurality of slots or serrations 1180 disposed in the inner surface. The slots and/or serrations 1180 may be laser cut, or formed by other methods. These serrations 1180 can be configured to facilitate bending to an engineered radius to facilitate formation of the region by the members.

The serrations 1180 may have any size, pattern, or shape. In some embodiments, the body 1110 may include different size serrations on each side to allow selection of larger or smaller fence sizes. The serrations 1180 can also facilitate uncurling in a way that will not disturb the delivered therapeutic material(s). The serrations may be of the same size and/or of different sizes along the length of the body.

Like FIG. 7, the device 1100 may include two steerable, bidirectional members 1132 and 1134 configured to magnetically connect to each other to define a barrier region in which one or more therapeutic materials may be delivered.

As shown in FIG. 11B, the body 1110 may include a plurality of lumens. In some embodiments, the body 1110 may include a lumen 1112 disposed in substantially the center of the body 1110 configured for a guide wire. In some embodiments, the body 1110 may include lumens 1114 and 1118 configured for the members 1132 and 1134, respectively. In some embodiments, the body 1110 may include two delivery lumens 1120 and 1122 configured for delivering the same therapeutic material and/or different therapeutic materials. The delivery lumens 1120 and 1122 may be disposed between the guide wire lumen 1112 and the lumens 1114 and 1118 for the members 1132 and 1134 so that the therapeutic material(s) can be delivered within the defined region. In some embodiments, the body 1110 may also include one or more lumens 1124 for sensors. For example, the one or more lumens 1124 may be for sensors for detecting electrical activity in the heart.

FIGS. 12A-12C show a delivery device 1200 including members 1232 and 1234 that are configured to expand radially with respect to the body 1210 to define a barrier region 1231. It will be understood that the delivery device 1200 are not limited two members as shown in the figures and the delivery device 1200 may also include additional members.

In some embodiments, the members 1232 and 1234 may be controllable collectively. In some embodiments, the members 1232 and 1234 may be configured to expand radially with respect to a guide wire 1202 disposed in a lumen substantially in the center of the body 1210 and configured to define the circular region 1231. The members 1232 and 1234 may be configured to be disposed in an elongate form (i.e., in line with the diameter of the body) when in unexpanded state, as shown in FIG. 12B.

In some embodiments, each of the members 1232 and 1234 may include lumens 1216 and 1218, respectively. In some embodiments, the device 1200 may include one or more steering members 1242 and 1244 disposed within the lumens 1216 and 1218, respectively, configured to control the radial expansion of the members 1232 and 1234, respectively, in the formation of the region 1231.

In some embodiments, each of the members 1232 and 1234 may include a plurality of ports 1236 configured to deliver one or more therapeutic materials and disposed on the internal surface (facing the region 1231). In some embodiments, each of the members 1232 and 1234 may include delivery lumens 1220 and 1222, respectively, configured to deliver the same therapeutic material(s) or different therapeutic materials.

As shown in FIG. 12C, the body 1210 may include a plurality of lumens. In some embodiments, the body 1210 may include a lumen 1212 disposed in substantially the center of the body 1210 configured for a guide wire 1202. In some embodiments, the body 1210 may include lumens 1214 and 1218 configured for the members 1232 and 1234, respectively.

In some embodiments, the delivery devices may be sterilized. In some embodiments, one, some, or all parts of the delivery devices may be reused. In further embodiments, one, some, or all parts of the delivery devices may be disposable. In further embodiments, the delivery devices may be a single, use device.

In some embodiments, the delivery devices may be part of a kit. In some embodiments, the kit may include the body, the one or more members, the one or more steering members, other components, a guide wire, or a combination thereof.

While the disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A device for delivering one or more therapeutic materials to a treatment site, comprising:
    a body;
    a member that is insertable with respect to the body and that is configured to connect to and/or overlap with respect to the member and/or the body to surround a barrier region at the treatment site, with the member being connected to and/or overlapped with respect to the member and/or the body along only a minority of a perimeter of the barrier region; and
    one or more delivery lumens configured to deliver the one or more therapeutic materials to the barrier region;
    wherein the member includes at least two sets of a plurality of delivery ports disposed on the member so that the at least two sets of delivery ports face the barrier region;
    wherein each set of delivery ports communicates with a delivery lumen of the one or more delivery lumens and is configured to deliver a therapeutic material of the one or more therapeutic materials within the barrier region; and
    wherein the body includes a set of first suction ports disposed on a distal end portion of the body and configured to deliver suction for stabilizing the body with respect to the treatment site.

2. The device of claim 1, wherein the member is configured to deploy from the body in an elongated state and transition to a connected and/or overlapped state.

3. The device of claim 1, wherein the member is configured to deploy in a connected state.

4. The device of claim 1, wherein:
    the member is configured to deploy with respect to the body in an elongated state and transition to an overlapped state in which a portion of the member is adjacent to another portion of the member after a length of the member is deployed; and
    in the overlapped state, the member surrounds the barrier region.

5. The device of claim 1, further comprising:
    one or more steering members configured to control movement of the member.

6. The device of claim 5, wherein the member and/or the one or more steering members are made of a shape memory material.

7. The device of claim 5, further comprising:
    a first connecting member disposed on one of the one or more steering members, the body, or the member; and
    a second connecting member disposed on another of the one or more steering members, the body, or the member;
    wherein the first connecting member and the second connecting member are configured to connect to one another.

8. The device of claim 1, wherein the at least two sets of a plurality of delivery ports comprises:
    a set of three or more first delivery ports disposed on the member so that the first delivery ports are arranged in a first plane; and
    a set of three or more second delivery ports disposed on the member so that the second delivery ports are arranged in a second plane that is spaced apart from and extends parallel to the first plane.

9. The device of claim 1, wherein a size of the barrier region is based on an amount of deployment of the member with respect to the body.

10. The device of claim 1, wherein the member includes one or more second suction ports configured to deliver suction.

11. A device for delivering one or more therapeutic materials to a treatment site, comprising:
    a body; and
    a member that is translatable with respect to the body and that is configured to surround a barrier region at the treatment site,
    wherein the member includes:
        a plurality of lumens;
        a set of first suction ports disposed on a first side of the member and so that the first suction ports face away from the barrier region, the first suction ports communicating with one or more first lumens of the plurality of lumens and being configured to deliver suction;
        a set of second suction ports disposed on a second side of the member opposite the first side and so that the second suction ports face away from the barrier region, the second suction ports communicating with the one or more first lumens and being configured to deliver suction; and
        at least one set of delivery ports disposed on the member between the first side and the second side and so that the delivery ports surround and face the barrier region, the delivery ports communicating with one or more second lumens of the plurality of lumens and being configured to deliver a therapeutic material of the one or more therapeutic materials within the barrier region while the first suction ports and the second suction ports deliver suction;
    wherein the body includes at least one set of third suction ports disposed on a distal end portion of the body and configured to deliver suction for stabilizing the body with respect to the treatment site.

12. The device of claim 11, wherein:
    the member is configured to deploy with respect to the body in an elongated state and transition to an overlapped state in which a portion of the member is adjacent to another portion of the member after a length of the member is deployed; and
    in the overlapped state, the member surrounds the barrier region.

13. The device of claim 11, further comprising:
    one or more steering members configured to control movement of the member.

14. The device of claim 13, wherein the member and/or the one or more steering members are made of a shape memory material.

15. The device of claim 13, further comprising:
a first connecting member disposed on one of the one or more steering members, the body, or the member; and
a second connecting member disposed on another of the one or more steering members, the body, or the member;
wherein the first connecting member and the second connecting member are configured to connect to one another.

16. The device of claim 11, wherein the barrier region is a circular shape region.

17. A method for delivering one or more therapeutic materials within a pericardium space, comprising:
advancing one or more members into the pericardium space through a body of a device;
forming a barrier region within the pericardium space by transitioning the one or more members with respect to the one or more members and/or the body from a disconnected or non-overlapped state to a connected or overlapped state so as to surround the barrier region;
delivering the one or more therapeutic materials to the barrier region via a plurality of delivery ports disposed on the one or more members so that the plurality of delivery ports face the barrier region;
maintaining the one or more members in the connected or overlapped state until the one or more therapeutic materials engraft or gelate within the barrier region; and
after the one or more therapeutic materials engraft or gelate within the barrier region, causing the one or more members to transition from the connected or overlapped state to the disconnected or non-overlapped state and be retracted with respect to the body.

18. The method of claim 17, wherein forming the barrier region further includes causing suction to be delivered through one or more suction ports disposed on the one or more members such that pericardial tissues and/or epicardial tissues adhere to the one or more members.

19. The method of claim 18, wherein delivering the one or more therapeutic materials to the barrier region comprises delivering the one or more therapeutic materials to the barrier region while suction is delivered through the one or more suction ports, and wherein the method further comprises:
prior to causing the one or more members to transition from the connected or overlapped state to the disconnected or non-overlapped state and be retracted with respect to the body, causing suction delivered through the one or more suction ports to be discontinued.

* * * * *